United States Patent
Beard et al.

(10) Patent No.: US 8,618,163 B2
(45) Date of Patent: Dec. 31, 2013

(54) DERIVATIVES OF CYCLOALKYL- AND CYCLOALKENYL-1,2-DICARBOXYLIC ACID COMPOUNDS HAVING FORMYL PEPTIDE RECEPTOR LIKE-1 (FPRL-1) AGONIST OR ANTAGONIST ACTIVITY

(75) Inventors: Richard L. Beard, Newport Beach, CA (US); John E. Donello, Dana Point, CA (US); Vidyasagar Vuligonda, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 133 days.

(21) Appl. No.: 13/168,464

(22) Filed: Jun. 24, 2011

(65) Prior Publication Data

US 2011/0319454 A1 Dec. 29, 2011

Related U.S. Application Data

(60) Provisional application No. 61/358,175, filed on Jun. 24, 2010.

(51) Int. Cl.
*A61K 31/21* (2006.01)
*A61K 31/16* (2006.01)
*A01N 37/18* (2006.01)

(52) U.S. Cl.
USPC ........... 514/510; 514/579; 514/613; 514/646; 514/656

(58) Field of Classification Search
USPC ................... 514/510, 579, 613, 646, 656
See application file for complete search history.

(56) References Cited

U.S. PATENT DOCUMENTS

| | | | |
|---|---|---|---|
| 3,998,621 A | 12/1976 | Pallos | |
| 4,166,452 A | 9/1979 | Generales, Jr. | |
| 4,256,108 A | 3/1981 | Theeuwes | |
| 4,265,874 A | 5/1981 | Bonsen | |
| 4,661,630 A | 4/1987 | Harigaya | |
| 2012/0190708 A1* | 7/2012 | Mackerell et al. | 514/301 |

FOREIGN PATENT DOCUMENTS

| | | |
|---|---|---|
| CH | 615911 | 2/1980 |
| WO | 03006425 | 1/2003 |
| WO | WO 2004089470 | 10/2004 |
| WO | 2010134014 | 11/2010 |

OTHER PUBLICATIONS

Angela Casini, Carbonic Anhydrase Inhibitors: Synthesis and Inhibition Against Isozymes I, II, and IV of Topically Acting Antiglaucoma Sulfonamides Incorporating cis-5-Norbornene-endo-3-Carboxy-2-Carboxamido Moieties, Overseas Publishers Association, 2001, 16, 113-123, J. Enzyme Inhibition.
Douglas Jabs, Guidelines for the use of Immunosuppressive Drugs in Patients With Ocular Inflammatory Disorders: Recommendations of an Expert Panel, Perspective, 2000, 130, 492-513, Am J Ophthalmol.
Gerard Bannenberg, Anti-Inflammatory Actions of Lipoxins, Department ofPlant Molecular Genetics, 2007, 17(6), 591-605, Expert Opin. Ther. Patents.

* cited by examiner

*Primary Examiner* — Renee Claytor
(74) *Attorney, Agent, or Firm* — Doina G. Ene

(57) ABSTRACT

The invention provides well defined compounds having FPRL-1 agonist or antagonist activity. As such, the compounds of the invention are useful for treating a variety of ocular disorders.

8 Claims, No Drawings

DERIVATIVES OF CYCLOALKYL- AND CYCLOALKENYL-1,2-DICARBOXYLIC ACID COMPOUNDS HAVING FORMYL PEPTIDE RECEPTOR LIKE-1 (FPRL-1) AGONIST OR ANTAGONIST ACTIVITY

RELATED APPLICATION

This application claims the benefit of U.S. Provisional Application Ser. No. 61/358,175, filed Jun. 24, 2010, the disclosure of which is hereby incorporated in its entirety herein by reference.

FIELD OF THE INVENTION

The present invention relates generally to compounds and methods for treating ocular disorders. The invention relates specifically to the use of certain well-defined compounds having formyl peptide receptor like-1 (FPRL-1) agonist or antagonist activity.

BACKGROUND OF THE INVENTION

FPRL-1 (N-formyl peptide receptor like-1) is a G protein-coupled receptor that is expressed on inflammatory cells such as monocytes and neutrophils, as well as T cells and has been shown to play a critical role in leukocyte trafficking during inflammation and human pathology. FPRL-1 is an exceptionally promiscuous receptor that responds to a large array of exogenous and endogenous ligands, including Serum amyloid A (SAA), chemokine variant sCKβ8-1, the neuroprotective peptide humanin, anti-inflammatory eicosanoid lipoxin A4 (LXA4) and glucocotricoid-modulated protein annexin A1. FPRL-1 transduces anti-inflammatory effects of LXA4 in many systems, but it also can mediate the pro-inflammatory signaling cascade of peptides such as SAA. The ability of the receptor to mediate two opposite effects is proposed to be a result of different receptor domains used by different agonists.

Activation of FPRL-1 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulate monocyte migration enabling clearance of apoptotic cells from the site of inflammation in a nonphlogistic manner. In addition, FPRL1 has been shown to inhibit NK cytotoxicity and promote activation of T cells which further contributes to down regulation of tissue damaging inflammatory signals. FPRL-1/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPRL-1 thus represents an important novel pro-resolutionary molecular target for the development of new therapeutic agents in diseases with excessive inflammatory responses.

SUMMARY OF THE INVENTION

The invention provides well defined compounds having FPRL-1 agonist or antagonist activity. As such, the compounds of the invention are useful for treating a variety of ocular disorders.

In one embodiment of the invention, there are provided methods for treating a disorder associated with mediation of a FPRL-1 receptor. Such methods can be performed, for example, by administering to a subject in need thereof a pharmaceutical composition containing a therapeutically effective amount of at least one compound of the structure:

Formula 1

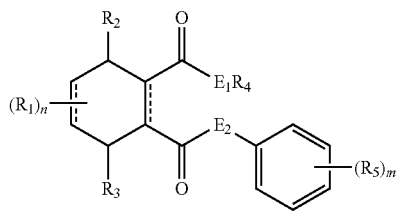

wherein:
a dashed line represents the presence or absence of a bond;
each $R_1$ is independently H, $C_1$-$C_6$ alkyl, $C_3$-$C_8$ cycloalkyl, or halide;
$R_2$ and $R_3$ are each independently H, $C_1$-$C_6$ alkyl, or $C_3$-$C_8$ cycloalkyl, or $R_2$ and $R_3$ taken together form a ring, wherein the ring optionally contains a heteroatom;
$R_4$ is H or $C_1$-$C_6$ alkyl;
each $R_5$ is independently H, alkyl, cycloalkyl, aryl, alkenyl, alkynyl, halide, hydroxy, alkoxy, trifluoromethyl, —$OCF_3$, nitroso, cyano, —$S(O)_2NH_2$, or —$C(O)OR_6$, wherein $R_6$ is H or $C_1$-$C_6$ alkyl;
$E_1$ is O or NH;
$E_2$ is O or $NR_5$, wherein $R_7$ is H or $C_1$-$C_6$ alkyl;
n is 0-2; and
m is 0-5;
or pharmaceutically acceptable salts, hydrates, solvates, crystal forms, isomers, tautomers, enantiomers, and diastereomers thereof.

In another embodiment of the invention there provided methods for treating a disorder associated with mediation of a FPRL-1 receptor. Such methods can be performed, for example, by administering to a subject in need thereof a pharmaceutical composition containing a therapeutically effective amount of at least one compound of the structure:

Formula 2

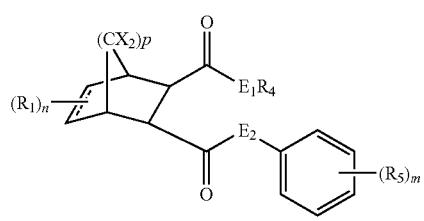

wherein:
a dashed line represents the presence or absence of a bond;
each $R_1$ is independently H, $C_1$-$C_6$ alkyl, $C_3$-$C_8$ cycloalkyl, or halide;
$R_2$ and $R_3$ are each independently H, $C_1$-$C_6$ alkyl, or $C_3$-$C_8$ cycloalkyl, or $R_2$ and $R_3$ taken together form a ring, wherein the ring optionally contains a heteroatom;
$R_4$ is H or $C_1$-$C_6$ alkyl;
each $R_5$ is independently H, $C_1$-$C_6$ alkyl, cycloalkyl, aryl, fused aryl, alkenyl, alkynyl, halide, hydroxy, alkoxy, trifluoromethyl, acetyl, —OCF$_3$, —SCF$_3$, nitroso, cyano, thioalkyl, —S(O)Me, —S(O)$_2$Me, —S(O)$_2$NH$_2$, or —C(O)OR$_6$, wherein R$_6$ is H or C$_1$-C$_6$ alkyl;

each X is independently H, C$_1$-C$_6$ alkyl, C$_1$-C$_6$ alkoxy, or each X taken together forms a cycloalkyl moiety, or each X taken together forms a substituted double bond;

E$_1$ is O or NH;

E$_2$ is O or NR$_5$, wherein R$_7$ is H or C$_1$-C$_6$ alkyl;

n is 0-2;

m is 0-5; and p is 1 or 2;

or pharmaceutically acceptable salts, hydrates, solvates, crystal forms, isomers, tautomers, enantiomers, and diastereomers thereof.

In still another embodiment of the invention, there are provided compounds of the structure:

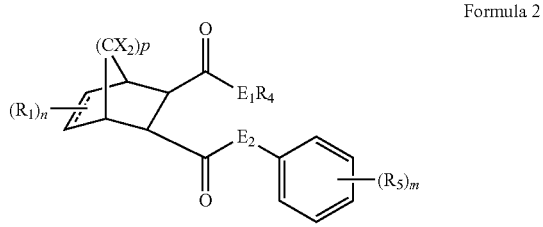

Formula 2 wherein:

a dashed line represents the presence or absence of a bond;

each R$_1$ is independently H, C$_1$-C$_6$ alkyl, C$_3$-C$_8$ cycloalkyl, or halide;

R$_2$ and R$_3$ are each independently H, C$_1$-C$_6$ alkyl, or C$_3$-C$_8$ cycloalkyl, or R$_2$ and R$_3$ taken together form a ring, wherein the ring optionally contains a heteroatom;

R$_4$ is H or C$_1$-C$_6$ alkyl;

each R$_5$ is independently H, C$_1$-C$_6$ alkyl, cycloalkyl, aryl, fused aryl, alkenyl, alkynyl, halide, hydroxy, alkoxy, trifluoromethyl, acetyl, —OCF$_3$, —SCF$_3$, nitroso, cyano, thioalkyl, —S(O)Me, —S(O)$_2$Me, —S(O)$_2$NH$_2$, or —C(O)OR$_6$, wherein R$_6$ is H or C$_1$-C$_6$ alkyl;

each X is independently H, C$_1$-C$_6$ alkyl, C$_1$-C$_6$ alkoxy, or each X taken together forms a cycloalkyl moiety, or each X taken together forms a substituted double bond;

E$_1$ is O or NH;

E$_2$ is O or NR$_5$, wherein R$_7$ is H or C$_1$-C$_6$ alkyl;

n is 0-2;

m is 0-5; and p is 1 or 2;

or pharmaceutically acceptable salts, hydrates, solvates, crystal forms, isomers, tautomers, enantiomers, and diastereomers thereof.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "C$_1$-C$_{100}$", refers to each integer in the given range; e.g., "C$_1$-C$_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)R$_7$, —CH$_2$OR$_7$, —C(O)—, —C(O)—, —S—, —S(O)$_2$, —OC(O)—O—, wherein R$_7$ is H or lower alkyl, acyl, oxyacyl, carboxyl, carbamate, sulfonyl, sulfonamide, sulfuryl, and the like. As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heterocyclic" refers to heterocyclic groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention. In addition, since certain compounds of the invention contain a norbornyl or norbornenyl moiety, all exo and endo isomers are contemplated for use in the practice of the invention.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

The invention provides methods for treating a disorder associated with mediation of a FPRL-1 receptor. Such methods are performed, for example, by administering to a subject in need thereof a pharmaceutical composition containing a therapeutically effective amount of at least one compound of the structure:

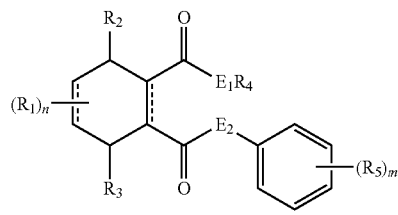

Formula 1 wherein:
  a dashed line represents the presence or absence of a bond;
  each $R_1$ is independently H, $C_1$-$C_6$ alkyl, $C_3$-$C_8$ cycloalkyl, or halide;
  $R_2$ and $R_3$ are each independently H, $C_1$-$C_6$ alkyl, or $C_3$-$C_8$ cycloalkyl, or $R_2$ and $R_3$ taken together form a ring, wherein the ring optionally contains a heteroatom;
  $R_4$ is H or $C_1$-$C_6$ alkyl;
  each $R_5$ is independently H, alkyl, cycloalkyl, aryl, alkenyl, alkynyl, halide, hydroxy, alkoxy, trifluoromethyl, —$OCF_3$, nitroso, cyano, —$S(O)_2NH_2$, or —$C(O)OR_6$, wherein $R_6$ is H or $C_1$-$C_6$ alkyl;

$E_1$ is O or NH;

$E_2$ is O or $NR_S$, wherein $R_7$ is H or $C_1$-$C_6$ alkyl;

n is 0-2; and m is 0-5;

or pharmaceutically acceptable salts, hydrates, solvates, crystal forms, isomers, tautomers, enantiomers, and diastereomers thereof.

In some embodiments of the invention, the compounds used in the methods of the invention are compounds wherein $E_2$ is $NR_7$ In some embodiments, the compounds used in the methods of the invention have the structure

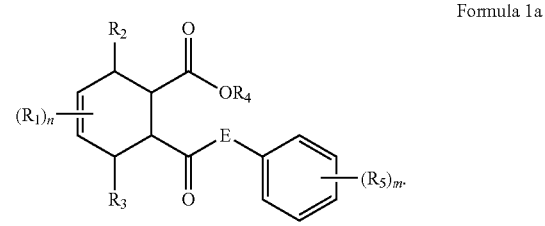

Formula 1a

In certain embodiments, $R_1$ is H, methyl, or Cl. In other embodiments of the invention, $R_2$ and $R_3$ are each independently H.

In some embodiments of the invention, the compounds used in the methods of the invention are compounds

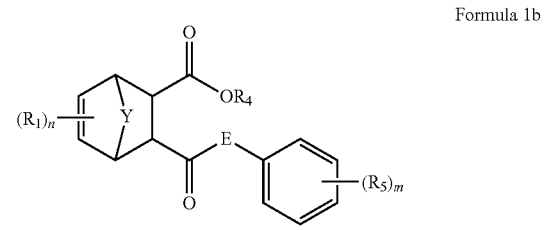

Formula 1b wherein Y is $CH_2$, O, $NR_7$, or S.

Compounds contemplated for use in the methods of the invention include, but are not limited to, compounds having the structures set forth below:

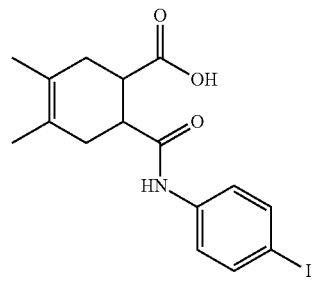

I

7
-continued
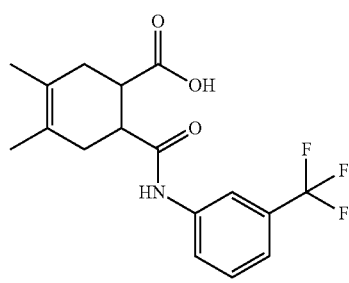
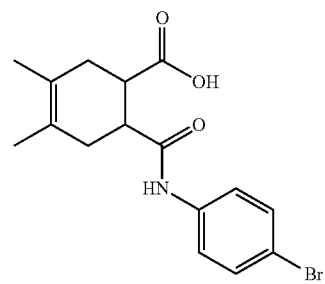
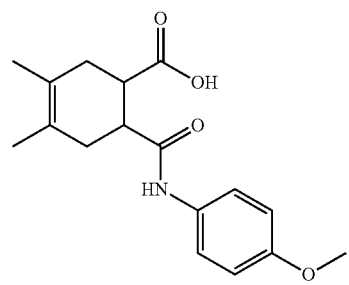
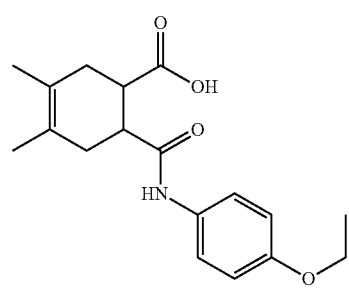
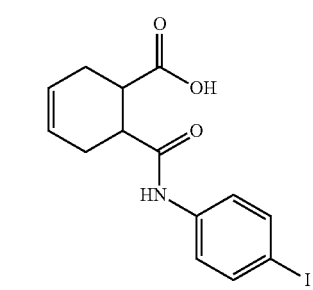
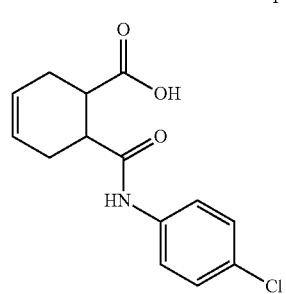
8
-continued
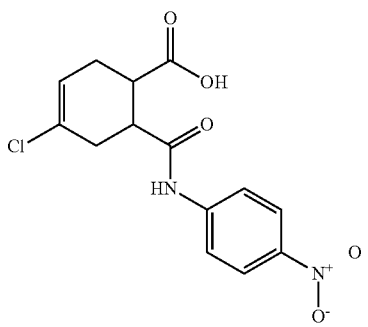
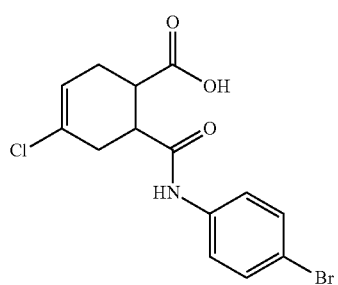
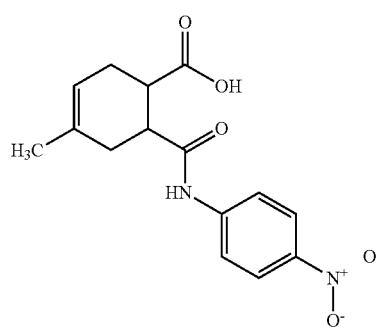
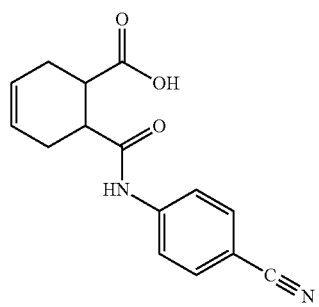
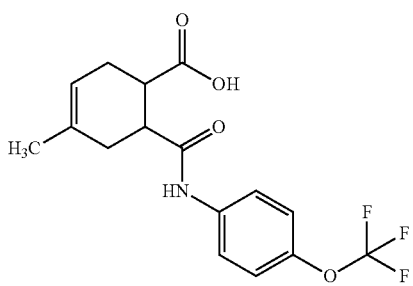

-continued

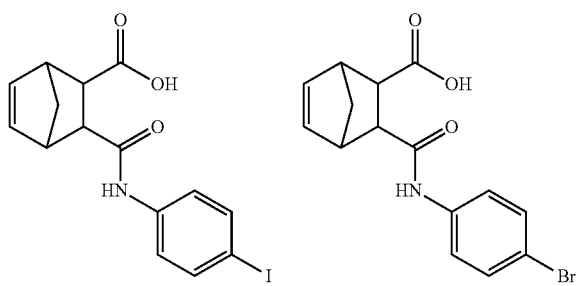

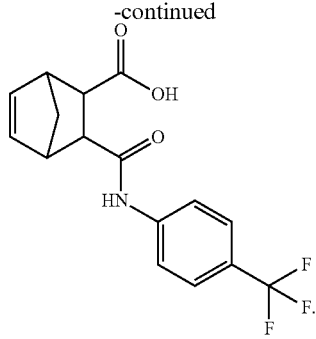

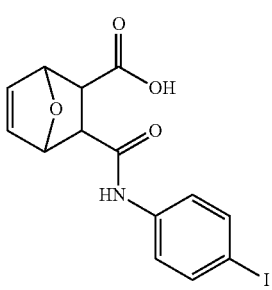

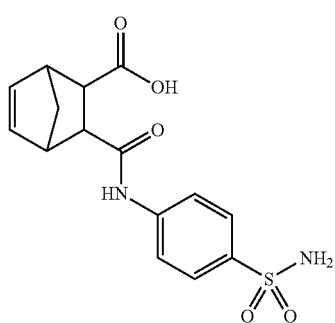

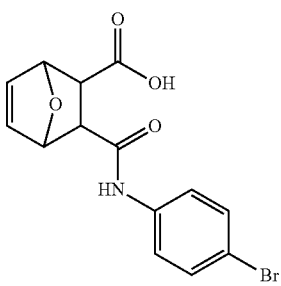

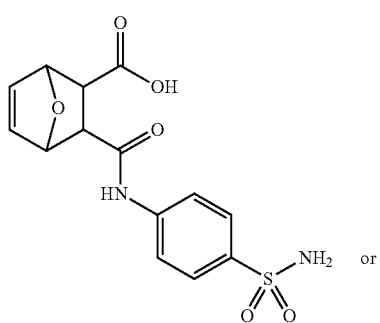 or

In another embodiment of the invention, there are provided methods for treating a disorder associated with mediation of a FPRL-1 receptor. Such methods can be performed for example, by administering to a subject in need thereof a pharmaceutical composition containing a therapeutically effective amount of at least one compound of the structure:

Formula 2

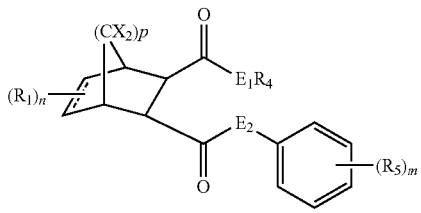

wherein:
a dashed line represents the presence or absence of a bond;
each $R_1$ is independently H, $C_1$-$C_6$ alkyl, $C_3$-$C_8$ cycloalkyl, or halide;
$R_2$ and $R_3$ are each independently H, $C_1$-$C_6$ alkyl, or $C_3$-$C_8$ cycloalkyl, or $R_2$ and $R_3$ taken together form a ring, wherein the ring optionally contains a heteroatom;
$R_4$ is H or $C_1$-$C_6$ alkyl;
each $R_5$ is independently H, $C_1$-$C_6$ alkyl, cycloalkyl, aryl, fused aryl, alkenyl, alkynyl, halide, hydroxy, alkoxy, trifluoromethyl, acetyl, —$OCF_3$, —$SCF_3$, nitroso, cyano, thioalkyl, —S(O)Me, —S(O)$_2$Me, —S(O)$_2NH_2$, or —C(O)$OR_6$, wherein $R_6$ is H or $C_1$-$C_6$ alkyl;
each X is independently H, $C_1$-$C_6$ alkyl, $C_1$-$C_6$ alkoxy, or each X taken together forms a cycloalkyl moiety, or each X taken together forms a substituted double bond;
$E_1$ is O or NH;
$E_2$ is O or $NR_7$, wherein $R_7$ is H or $C_1$-$C_6$ alkyl;
n is 0-2;
m is 0-5; and
p is 1 or 2;
or pharmaceutically acceptable salts, hydrates, solvates, crystal forms, isomers, tautomers, enantiomers, and diastereomers thereof.

In some embodiments of the invention, the compounds used in the methods of the invention are compounds wherein $E_2$ is $NR_7$.

In some embodiments of the invention, the compounds used in the methods of the invention are compounds having the structures Formula 2a

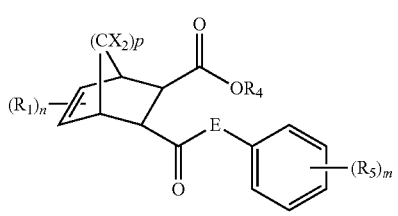

Formula 2b

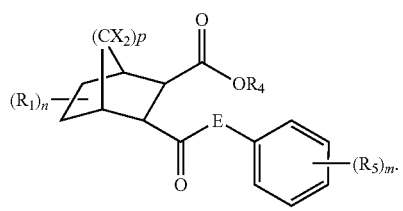

In some embodiments of the invention, the compounds used in the methods of the invention are compounds wherein $R_5$ is H, $C_1$-$C_6$ alkyl, halide, or trifluoromethyl In certain embodiments of the invention, the compounds used in the methods of the invention are compounds wherein each X taken together forms a cyclopropyl moiety.

Compounds contemplated for use according to this aspect of the invention include, but are not limited to, compounds having the structures set forth below:

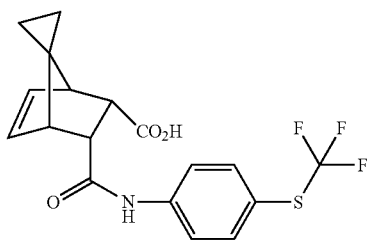

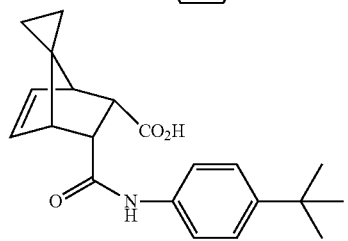

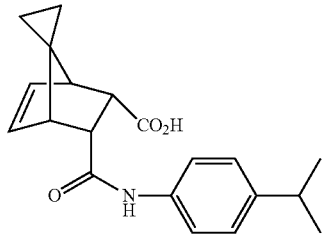

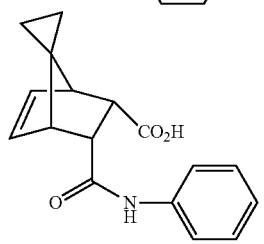

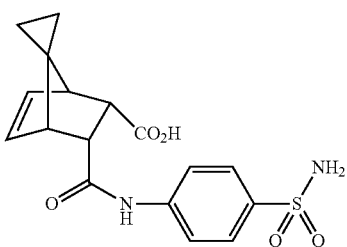

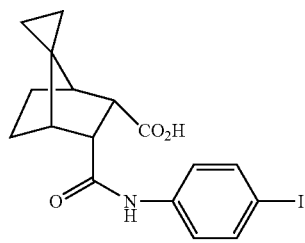

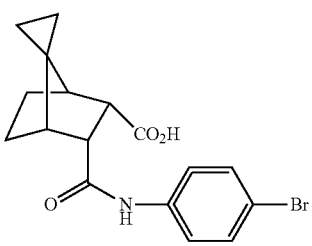

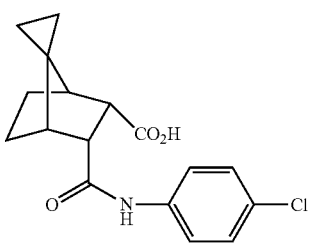

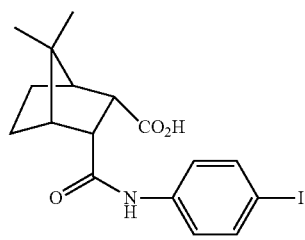

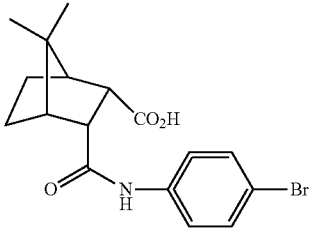

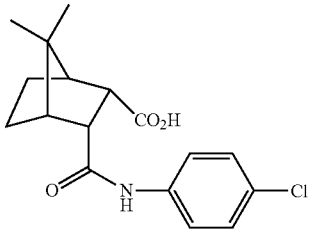

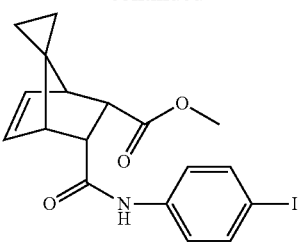

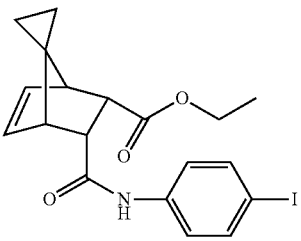

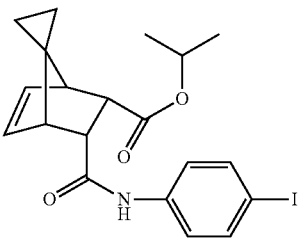

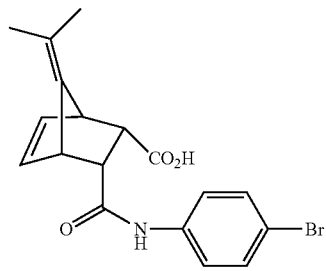

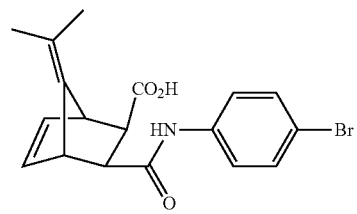

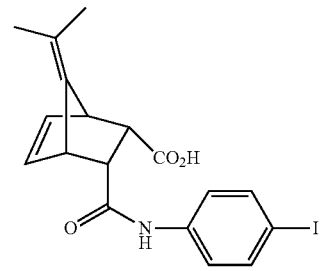

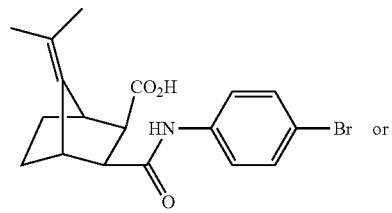

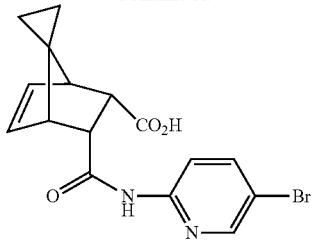

In a further embodiment of the invention there are provided compounds of the structure:

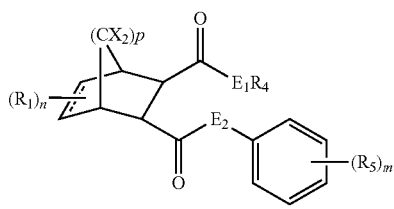

Formula 2 wherein:
- a dashed line represents the presence or absence of a bond;
- each $R_1$ is independently H, $C_1$-$C_6$ alkyl, $C_3$-$C_8$ cycloalkyl, or halide;
- $R_2$ and $R_3$ are each independently H, $C_1$-$C_6$ alkyl, or $C_3$-$C_8$ cycloalkyl, or $R_2$ and $R_3$ taken together form a ring, wherein the ring optionally contains a heteroatom;
- $R_4$ is H or $C_1$-$C_6$ alkyl;
- each $R_5$ is independently H, $C_1$-$C_6$ alkyl, cycloalkyl, aryl, fused aryl, alkenyl, alkynyl, halide, hydroxy, alkoxy, trifluoromethyl, acetyl, —$OCF_3$, —$SCF_3$, nitroso, cyano, thioalkyl, —S(O)Me, —S(O)$_2$Me, —S(O)$_2$NH$_2$, or —C(O)OR$_6$, wherein $R_6$ is H or $C_1$-$C_6$ alkyl;
- each X is independently H, $C_1$-$C_6$ alkyl, $C_1$-$C_6$ alkoxy, or each X taken together forms a cycloalkyl moiety, or each X taken together forms a substituted double bond;
- $E_1$ is O or NH;
- $E_2$ is O or NR$_S$, wherein $R_7$ is H or $C_1$-$C_6$ alkyl;
- n is 0-2;
- m is 0-5; and
- p is 1 or 2;

or pharmaceutically acceptable salts, hydrates, solvates, crystal forms, isomers, tautomers, enantiomers, and diastereomers thereof.

In certain embodiments, $E_2$ is NR$_7$.

In other embodiments, there are provided compounds of the structure

Formula 2a
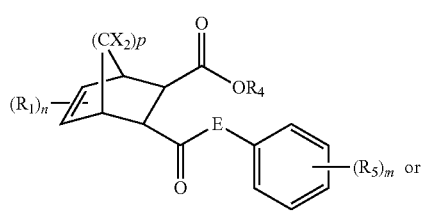
Formula 2b
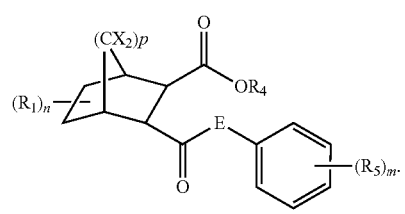
In some embodiments of the invention, $R_5$ is H, $C_1$-$C_6$ alkyl, halide, or trifluoromethyl
In certain embodiments, each X taken together forms a cyclopropyl moiety.
Compounds contemplated in this aspect of the invention include, but are not limited to, compounds having any one of the structures
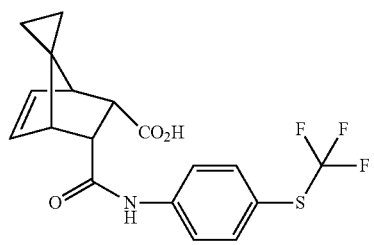
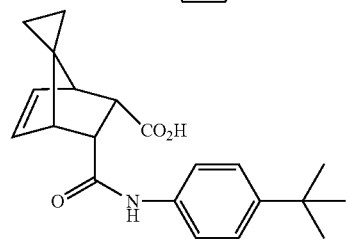
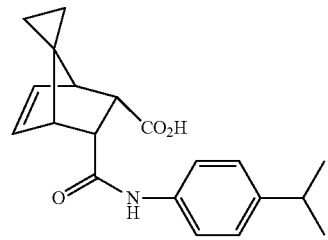
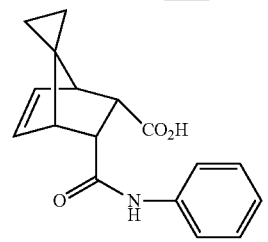
-continued
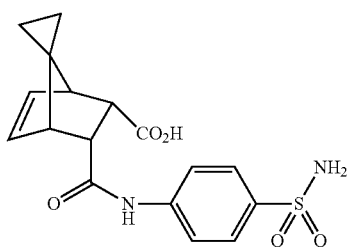
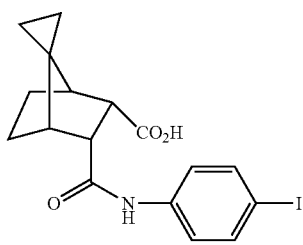
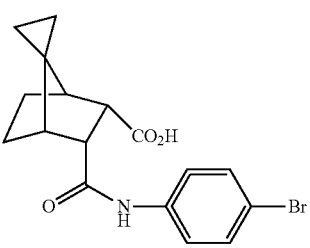
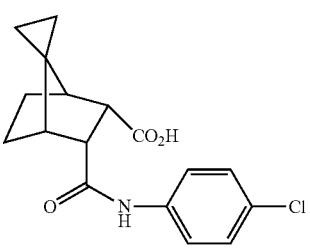
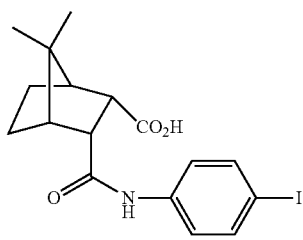
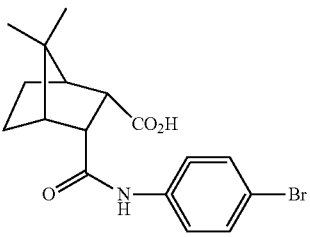
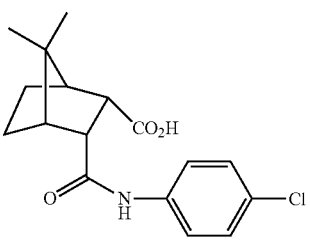

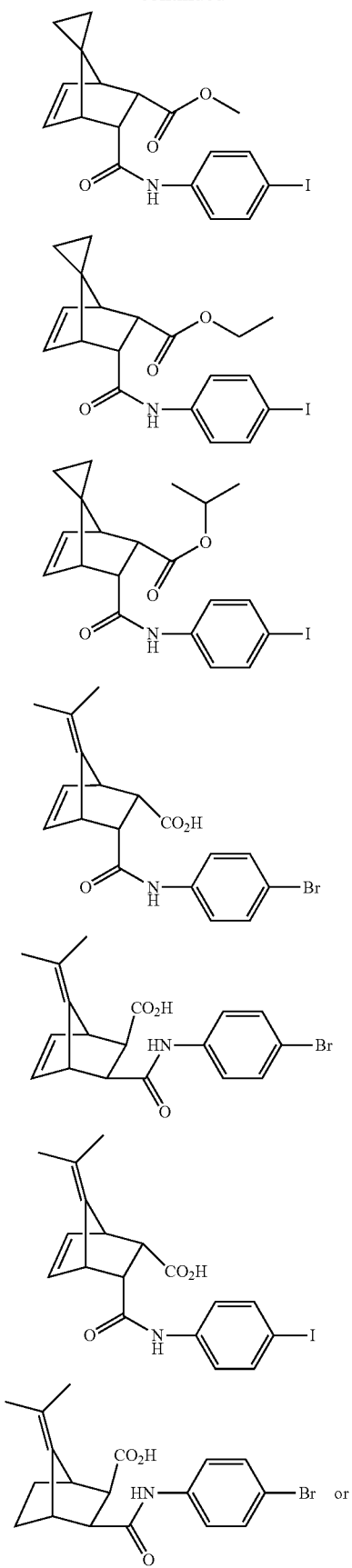
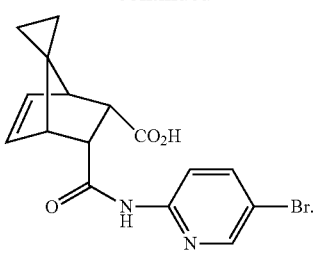
The compounds of the invention may be prepared in a variety of ways. One method for preparing invention compounds is set forth in the schematic set forth below:
Scheme 1. Preparation of starting materials.
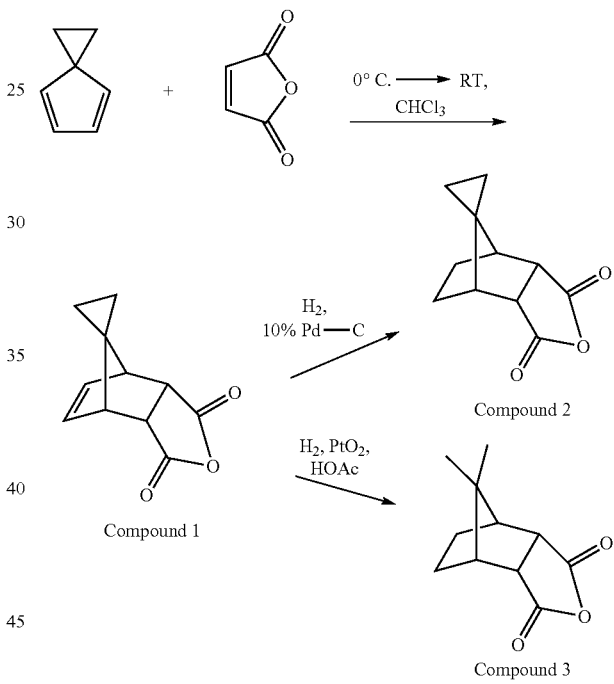
Scheme 2. General Procedure A
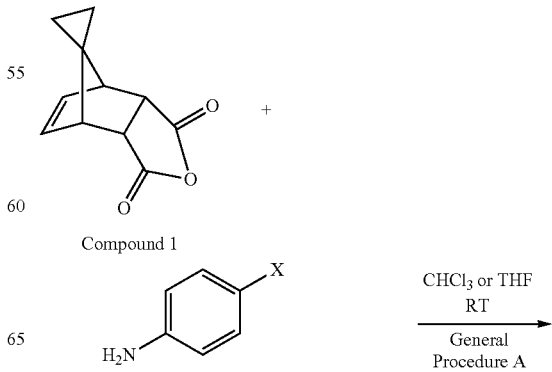

-continued

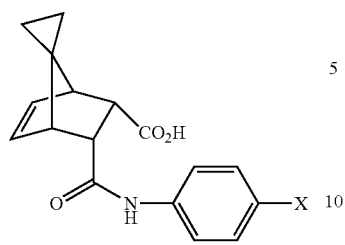

Compound 4 (X = SCF₃)
Compound 5 (X = t-Bu)
Compound 6 (X = i-Pr)
Compound 7 (X = H)
Compound 8 (X = SO₂NH₂)
Compound 15 (X = I)

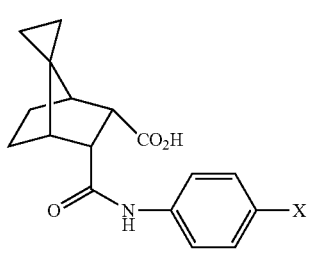

Compound 9 (X = I)
Compound 10 (X = Br)
Compound 11 (X = Cl)

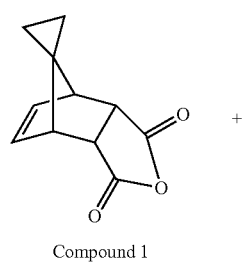 +

Compound 1

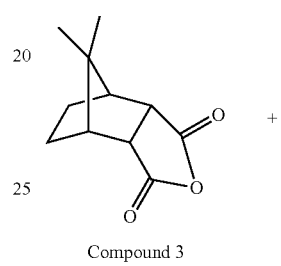 +

Compound 3

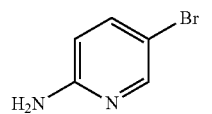 $\xrightarrow{\text{THF, 70° C.}}$ General Procedure A

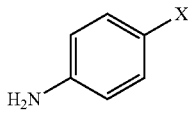 $\xrightarrow{\text{CHCl}_3\text{, RT}}$ General Procedure A

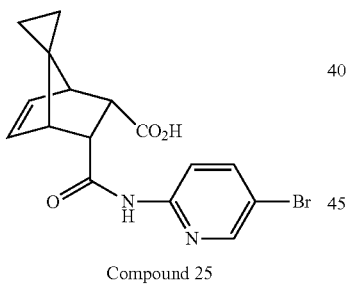

Compound 25

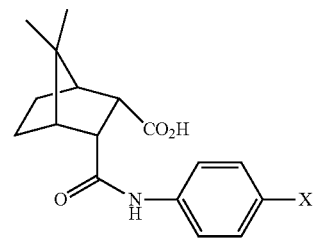

Compound 12 (X = I)
Compound 13 (X = Br)
Compound 14 (X = Cl)

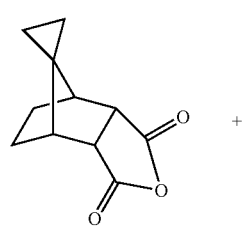 +

Compound 2

Scheme 3. General Procedure B

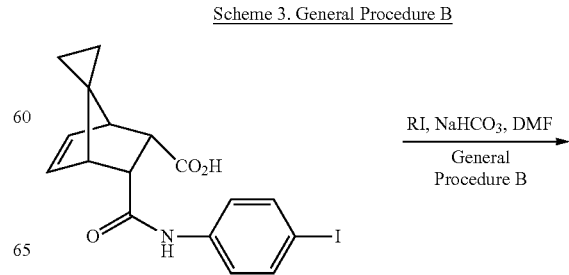 $\xrightarrow{\text{RI, NaHCO}_3\text{, DMF}}$ General Procedure B

H₂N—⟨X⟩ $\xrightarrow{\text{CHCl}_3\text{, RT}}$ General Procedure A

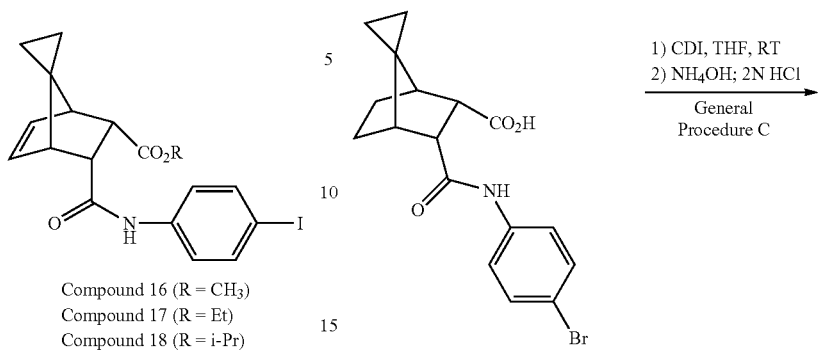
Scheme 5. General Procedure C
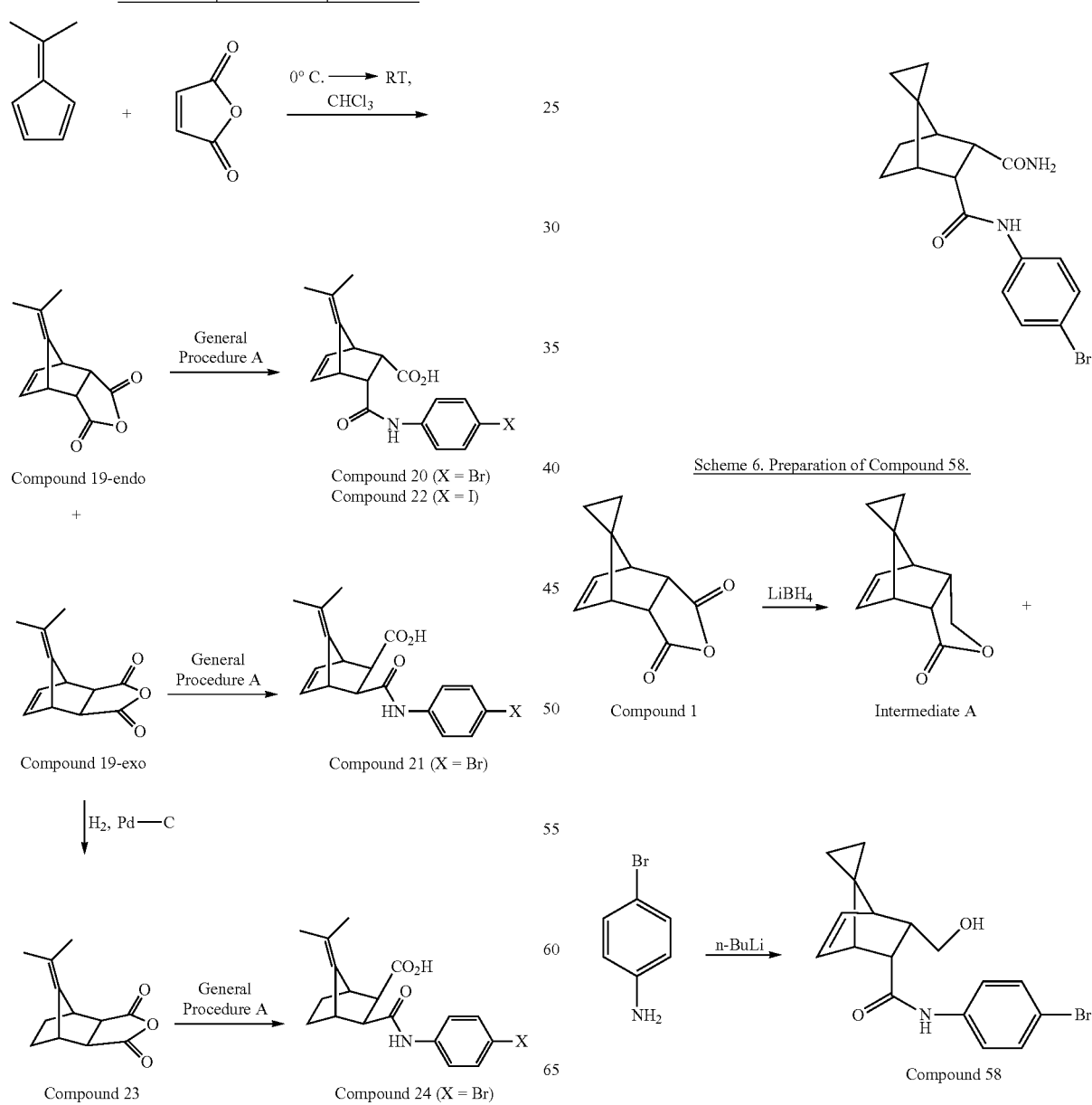

Scheme 7. Preparation of Compound 59.

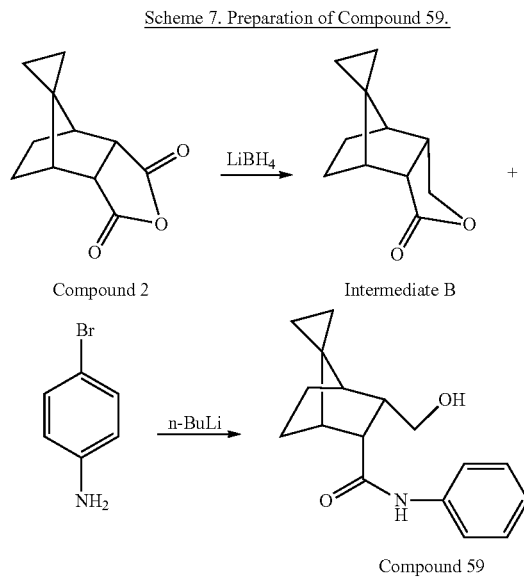

Biological activity of compounds according to Formula 1 and Formula 2 is set forth in Table 1 below. CHO-Gal6 cells stably expressing FPRL1 were cultured in (F12, 10% FBS, 1% PSA, 400 μg/ml geneticin and 50 μg/ml hygromycin) and HEK-Gqi5 cells stable expressing FPR1 were cultured in (DMEM high glucose, 10% FBS, 1% PSA, 400 μg/ml geneticin and 50 μg/ml hygromycin). In general, the day before the experiment, 18,000 cells/well were plated in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as $EC_{50}$ (nM) and efficacy values.

TABLE 1

| Compound Number | Structure | FPRL1 $EC_{50}$ (rel. eff.) | FPR1 $EC_{50}$ (rel. eff.) |
|---|---|---|---|
| 4 | 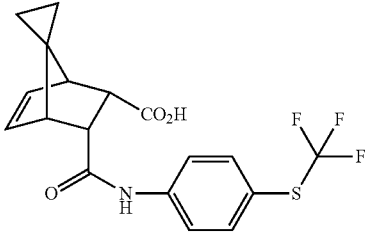 [SMILES: O=C(O)C1C(C(=O)Nc2ccc(SC(F)(F)F)cc2)C2C=CC1C21CC1] | 709 nM (0.84) | NA |
| 5 | 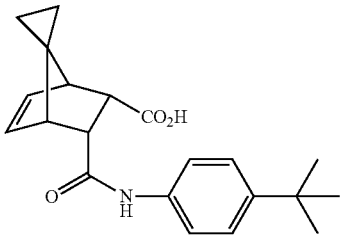 [SMILES: CC(C)(C)c1ccc(NC(=O)C2C(C(=O)O)C3C=CC2C32CC2)cc1] | NA | NA |
| 6 | 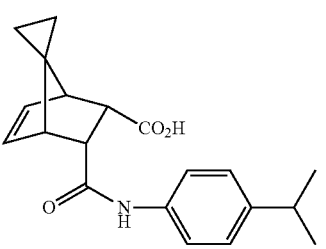 [SMILES: CC(C)c1ccc(NC(=O)C2C(C(=O)O)C3C=CC2C32CC2)cc1] | ND (0.39) | NA |

TABLE 1-continued

| Compound Number | Structure | FPRL1 EC$_{50}$ (rel. eff.) | FPR1 EC$_{50}$ (rel. eff.) |
| --- | --- | --- | --- |
| 7 | 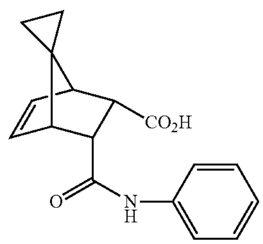 [SMILES: O=C(O)C1C(C(=O)Nc2ccccc2)C2C=CC1C21CC1] | ND (0.33) | NA |
| 8 | 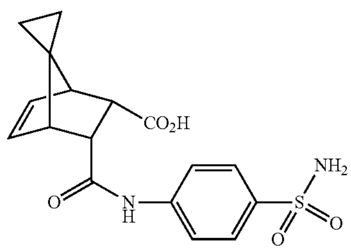 [SMILES: NS(=O)(=O)c1ccc(NC(=O)C2C(C(=O)O)C3C=CC2C32CC2)cc1] | 2706 nM (0.51) | NA |
| 9 | 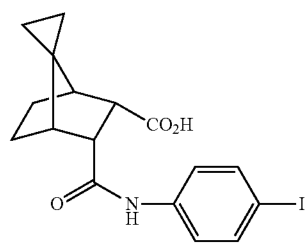 | 1 nM (0.80) | 269 nM (0.73) |
| 10A | (−)-isomer | 278 nM (0.82) | NA |
| 10B | (+)-isomer | <1 nM (0.98) | 2172 nM (0.76) |

TABLE 1-continued

| Compound Number | Structure | FPRL1 EC$_{50}$ (rel. eff.) | FPR1 EC$_{50}$ (rel. eff.) |
|---|---|---|---|
| 11 | 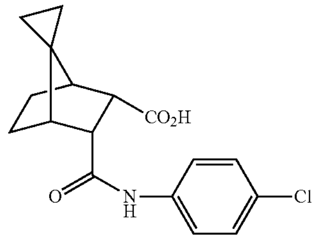 [SMILES: O=C(O)C1C(C(=O)Nc2ccc(Cl)cc2)C2CCC1C21CC1] | 43 nM (0.86) | ND |
| 12 | 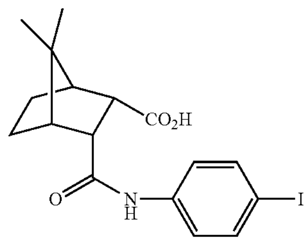 [SMILES: CC1(C)C2CCC1C(C(=O)Nc1ccc(I)cc1)C2C(=O)O] | 1.7 nM (0.97) | 343 nM (68) |
| 13 | 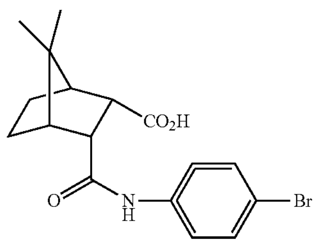 | 10 nM (0.85) | 639 nM (0.33) |
| 14 | 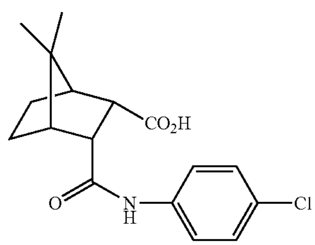 [SMILES: CC1(C)C2CCC1C(C(=O)Nc1ccc(Cl)cc1)C2C(=O)O] | 36 nM (0.86) | NA |
| 16 | 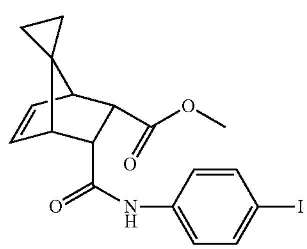 [SMILES: COC(=O)C1C(C(=O)Nc2ccc(I)cc2)C2C=CC1C21CC1] | 403 nM (0.72) | ND |
| 17 | 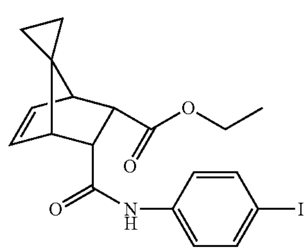 [SMILES: CCOC(=O)C1C(C(=O)Nc2ccc(I)cc2)C2C=CC1C21CC1] | 243 nM (0.76) | NA |

TABLE 1-continued
| Compound Number | Structure | FPRL1 EC$_{50}$ (rel. eff.) | FPR1 EC$_{50}$ (rel. eff.) |
|---|---|---|---|
| 18 | 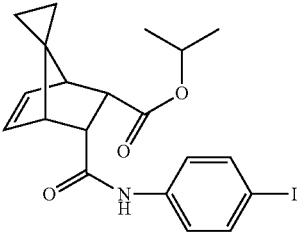 [SMILES: CC(C)OC(=O)C1C(C(=O)Nc2ccc(I)cc2)C2C=CC1C21CC1] | 187 nM (0.72) | NA |
| 20 | 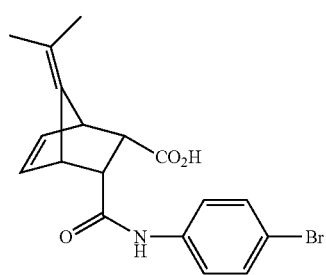 [SMILES: CC(C)=C1C2C=CC1C(C(=O)Nc1ccc(Br)cc1)C2C(=O)O] | 30 nM (0.96) | NA |
| 21 | 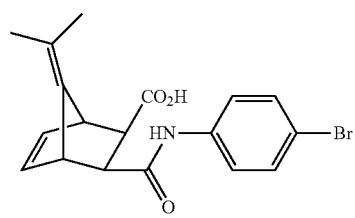 [SMILES: CC(C)=C1C2C=CC1C(C(=O)Nc1ccc(Br)cc1)C2C(=O)O] | 461 nM (0.77) | 10000 nM (50) |
| 22 | 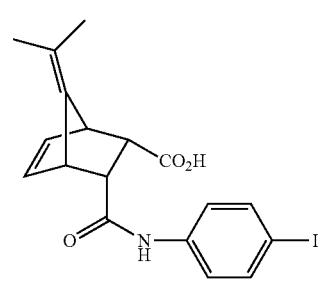 [SMILES: CC(C)=C1C2C=CC1C(C(=O)Nc1ccc(I)cc1)C2C(=O)O] | 11 nM (88) | 8027 nM (62) |
| 24 | 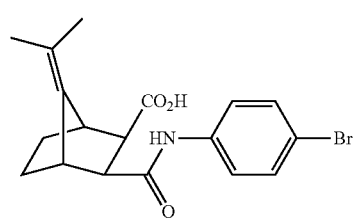 [SMILES: CC(C)=C1C2CCC1C(C(=O)Nc1ccc(Br)cc1)C2C(=O)O] | 164 nM (0.89) | 8300 nM (41) |
| 25 | 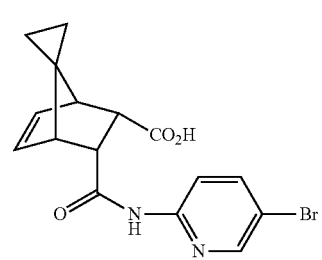 [SMILES: O=C(O)C1C(C(=O)Nc2ccc(Br)cn2)C2C=CC1C21CC1] | 149 nM (0.74) | NA |

TABLE 1-continued

| Compound Number | Structure | FPRL1 EC$_{50}$ (rel. eff.) | FPR1 EC$_{50}$ (rel. eff.) |
| --- | --- | --- | --- |
| 26 | 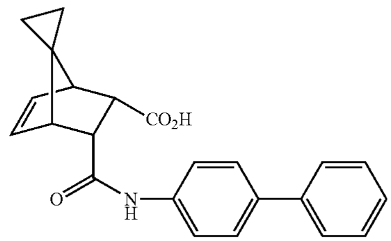 [SMILES: O=C(O)C1C(C(=O)Nc2ccc(-c3ccccc3)cc2)C2C=CC1C21CC1] | 2360 nM (0.69) | NA |
| 27 | 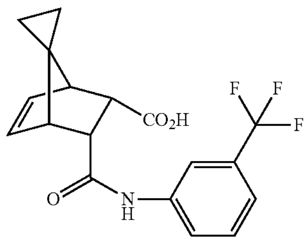 [SMILES: O=C(O)C1C(C(=O)Nc2cccc(C(F)(F)F)c2)C2C=CC1C21CC1] | 2770 nM (0.72) | NA |
| 28 | 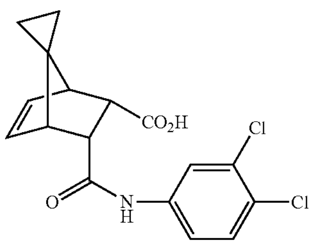 [SMILES: O=C(O)C1C(C(=O)Nc2ccc(Cl)c(Cl)c2)C2C=CC1C21CC1] | 616 nM (0.70) | NA |
| 29 | 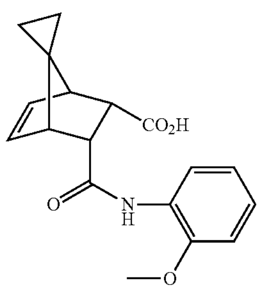 [SMILES: COc1ccccc1NC(=O)C1C(C(=O)O)C2C=CC1C21CC1] | 3167 nM (1.1) | ND |
| 30 | 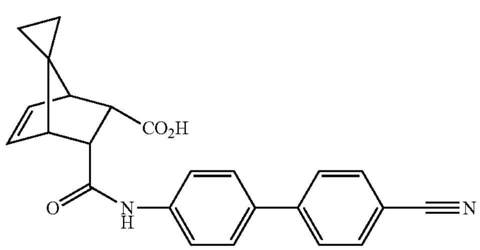 [SMILES: N#Cc1ccc(-c2ccc(NC(=O)C3C(C(=O)O)C4C=CC3C43CC3)cc2)cc1] | 2885 nM (0.97) | ND |
| 31 | 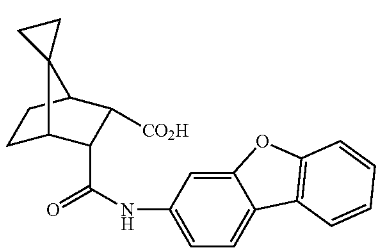 [SMILES: O=C(O)C1C(C(=O)Nc2ccc3c(c2)oc2ccccc23)C2CCC1C21CC1] | 2255 nM (0.9) | NA |

TABLE 1-continued

| Compound Number | Structure | FPRL1 EC$_{50}$ (rel. eff.) | FPR1 EC$_{50}$ (rel. eff.) |
|---|---|---|---|
| 32 | 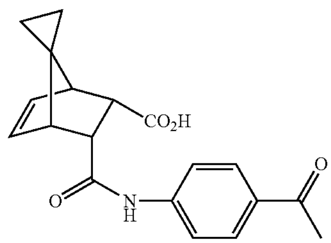 [SMILES: CC(=O)c1ccc(NC(=O)C2C(C(=O)O)C3C=CC2C32CC2)cc1] | 277 nM (0.96) | NA |
| 33 | 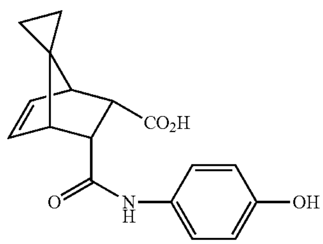 [SMILES: O=C(O)C1C(C(=O)Nc2ccc(O)cc2)C2C=CC1C21CC1] | NA | NA |
| 34 | 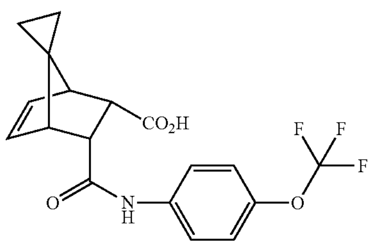 | 585 nM (0.96) | NA |
| 35 | 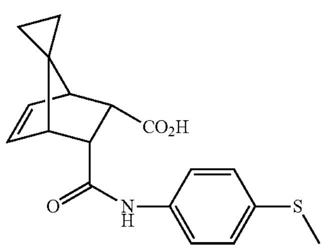 [SMILES: CSc1ccc(NC(=O)C2C(C(=O)O)C3C=CC2C32CC2)cc1] | 14 nM (0.85) | NA |
| 36 | 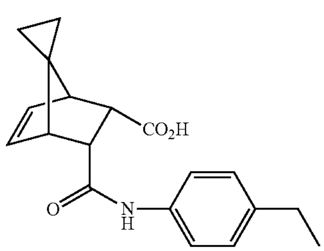 | 59 nM (0.91) | NA |
| 37 | 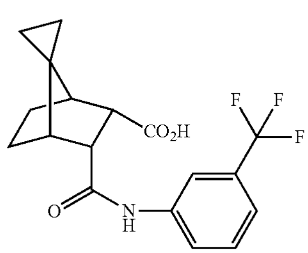 [SMILES: O=C(O)C1C(C(=O)Nc2cccc(C(F)(F)F)c2)C2CCC1C21CC1] | 978 nM (0.86) | ND |

TABLE 1-continued

| Compound Number | Structure | FPRL1 EC$_{50}$ (rel. eff.) | FPR1 EC$_{50}$ (rel. eff.) |
| --- | --- | --- | --- |
| 38 | 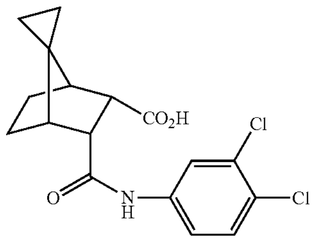 [SMILES: O=C(O)C1C(C(=O)Nc2ccc(Cl)c(Cl)c2)C2CCC1C21CC1] | 498 nM (1.00) | ND |
| 39 | 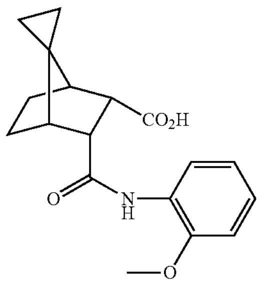 [SMILES: COc1ccccc1NC(=O)C1C(C(=O)O)C2CCC1C21CC1] | >3000 nM (1.2) | ND |
| 40 | 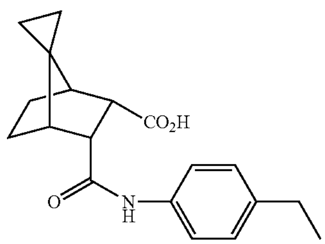 [SMILES: CCc1ccc(NC(=O)C2C(C(=O)O)C3CCC2C32CC2)cc1] | 16 nM (0.79) | NA |
| 41 | 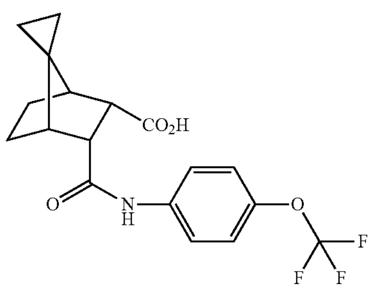 [SMILES: O=C(O)C1C(C(=O)Nc2ccc(OC(F)(F)F)cc2)C2CCC1C21CC1] | 123 nM (0.80) | NA |
| 42 | 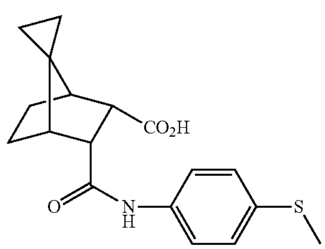 [SMILES: CSc1ccc(NC(=O)C2C(C(=O)O)C3CCC2C32CC2)cc1] | 7 nM (0.96) | 1101 nM (0.23) |
| 43 | 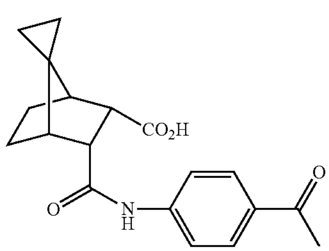 [SMILES: CC(=O)c1ccc(NC(=O)C2C(C(=O)O)C3CCC2C32CC2)cc1] | 49 nM (0.71) | >10 μM (0.50) |

TABLE 1-continued

| Compound Number | Structure | FPRL1 EC$_{50}$ (rel. eff.) | FPR1 EC$_{50}$ (rel. eff.) |
| --- | --- | --- | --- |
| 44 | 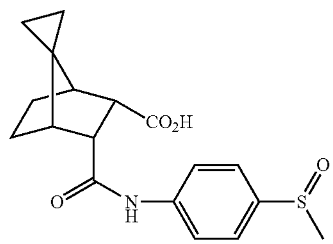 [SMILES: CS(=O)c1ccc(NC(=O)C2C(C(=O)O)C3CCC2C32CC2)cc1] | 475 nM (0.95) | NA |
| 45 | 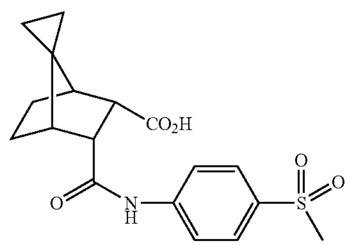 [SMILES: CS(=O)(=O)c1ccc(NC(=O)C2C(C(=O)O)C3CCC2C32CC2)cc1] | 598 nM (0.86) | NA |
| 46A | (+)-isomer | 6523 nM (0.85) | NA |
| 46B | (−)-isomer | <1 nM (0.91) | >40 μM (0.30) |
| 47 | 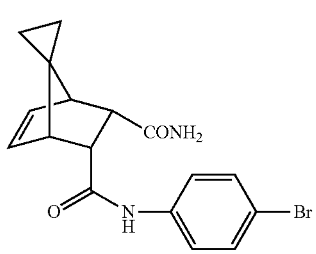 [SMILES: NC(=O)C1C(C(=O)Nc2ccc(Br)cc2)C2C=CC1C21CC1] | 4.8 nM (0.91) | NA |

TABLE 1-continued

| Compound Number | Structure | FPRL1 EC$_{50}$ (rel. eff.) | FPR1 EC$_{50}$ (rel. eff.) |
| --- | --- | --- | --- |
| 48 | 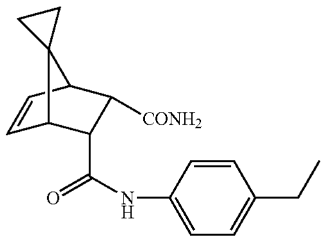 [SMILES: CCc1ccc(NC(=O)C2C(C(N)=O)C3C=CC2C32CC2)cc1] | 51 nM (0.79) | NA |
| 49 | 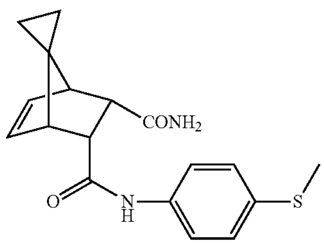 | 97 nM (0.90) | NA |
| 50 | 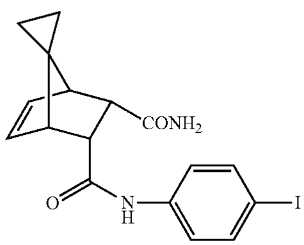 [SMILES: NC(=O)C1C(C(=O)Nc2ccc(I)cc2)C2C=CC1C21CC1] | 1.8 nM (0.85) | NA |
| 51 | 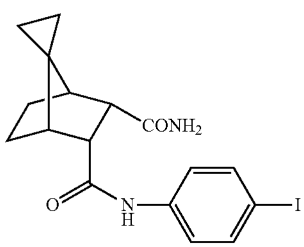 [SMILES: NC(=O)C1C(C(=O)Nc2ccc(I)cc2)C2CCC1C21CC1] | <4.8 nM (0.87) | NA |
| 52 | 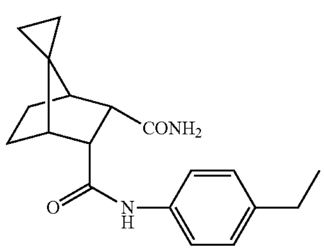 | 33 nM (0.97) | NA |
| 53 | 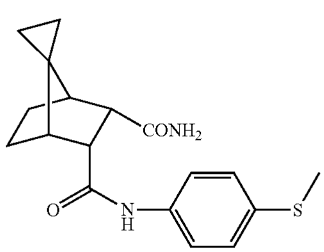 | 15 nM (0.86) | NA |

TABLE 1-continued
| Compound Number | Structure | FPRL1 EC$_{50}$ (rel. eff.) | FPR1 EC$_{50}$ (rel. eff.) |
|---|---|---|---|
| 54 | 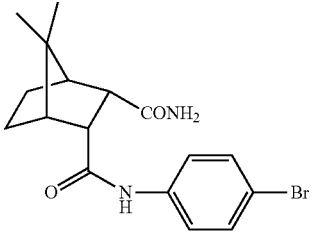 [SMILES: CC1(C)C2CCC1C(C(=O)Nc1ccc(Br)cc1)C2C(N)=O] | 15 nM (0.77) | NA |
| 55 | 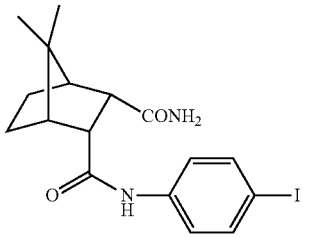 | 2.6 nM (0.81) | NA |
| 56 | 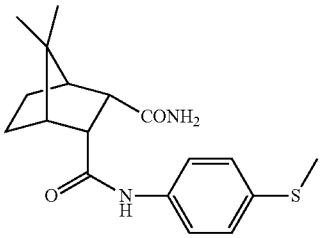 [SMILES: CSc1ccc(NC(=O)C2C(C(N)=O)C3CCC2C3(C)C)cc1] | ND (0.96) | NA |
| 57 | 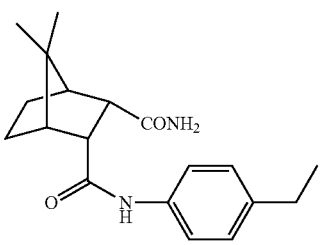 [SMILES: CCc1ccc(NC(=O)C2C(C(N)=O)C3CCC2C3(C)C)cc1] | 35 nM (0.95) | NA |
| 58 | 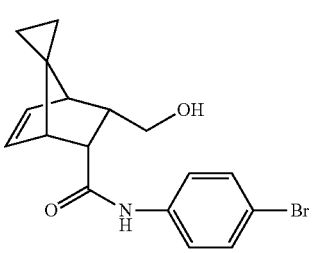 [SMILES: O=C(Nc1ccc(Br)cc1)C1C(CO)C2C=CC1C21CC1] | 229 nM (0.91) | NA |
| 59 | 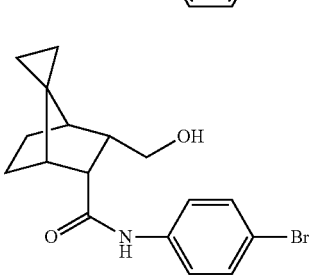 | >10 μM (0.76) | NA |

TABLE 1-continued

| Compound Number | Structure | FPRL1 EC$_{50}$ (rel. eff.) | FPR1 EC$_{50}$ (rel. eff.) |
|---|---|---|---|
| 60 | 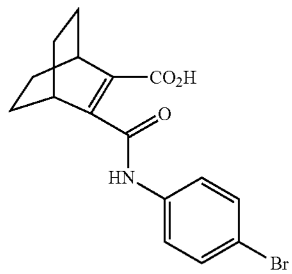 [SMILES: O=C(O)C1=C(C(=O)Nc2ccc(Br)cc2)C2CCC1CC2] | 143 nM (1.0) | NA |
| 61 | 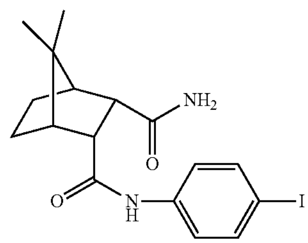 [SMILES: CC1(C)C2CCC1C(C(=O)Nc1ccc(I)cc1)C2C(N)=O] | 2.7 nM (0.82) | NA |
| 62 | 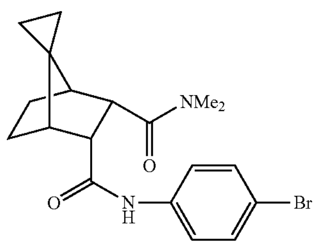 | 5.0 (0.89) | NA |
| 63 | 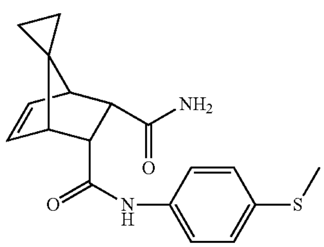 | 96.6 (0.9) | NA |
| 64 | 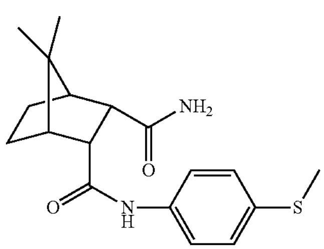 [SMILES: CSc1ccc(NC(=O)C2C(C(N)=O)C3CCC2C3(C)C)cc1] | 17.2 (0.9) | NA |
| 65 | 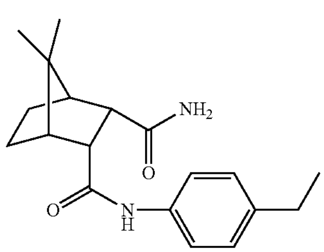 [SMILES: CCc1ccc(NC(=O)C2C(C(N)=O)C3CCC2C3(C)C)cc1] | 35 (0.95) | NA |

TABLE 1-continued

| Compound Number | Structure | FPRL1 EC$_{50}$ (rel. eff.) | FPR1 EC$_{50}$ (rel. eff.) |
|---|---|---|---|
| 66 | 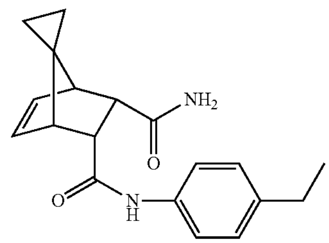 [SMILES: CCc1ccc(NC(=O)C2C(C(N)=O)C3C=CC2C32CC2)cc1] | 50.8 (0.79) | NA |
| 67 | 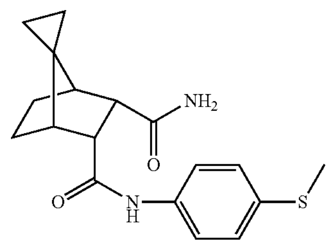 | 15.7 (0.91) | NA |
| 68 | 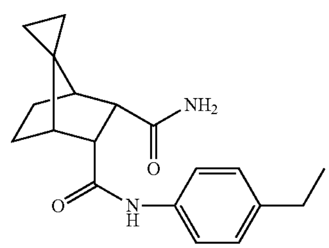 [SMILES: CSc1ccc(NC(=O)C2C(C(N)=O)C3CCC2C32CC2)cc1] | 38.1 (1.0) | NA |
| 69 | 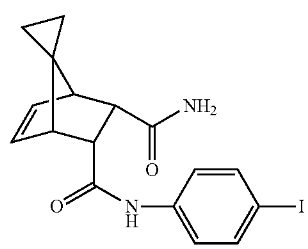 [SMILES: NC(=O)C1C(C(=O)Nc2ccc(I)cc2)C2C=CC1C21CC1] | 7.7 (0.87) | NA |
| 70 | 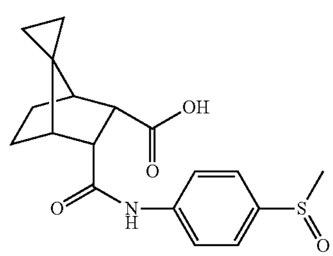 [SMILES: CS(=O)c1ccc(NC(=O)C2C(C(=O)O)C3CCC2C32CC2)cc1] | 474.9 (0.95) | NA |
| 71 | 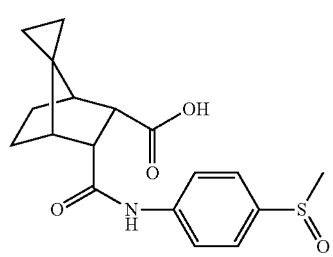 [SMILES: CS(=O)c1ccc(NC(=O)C2C(C(=O)O)C3CCC2C32CC2)cc1] | 598 (0.86) | NA |

TABLE 1-continued

| Compound Number | Structure | FPRL1 EC$_{50}$ (rel. eff.) | FPR1 EC$_{50}$ (rel. eff.) |
| --- | --- | --- | --- |
| 72 | 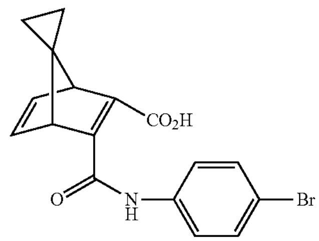 [SMILES: O=C(O)C1=C(C(=O)Nc2ccc(Br)cc2)C2C=CC1C21CC1] | 617 (0.92) | NA |
| 73 | 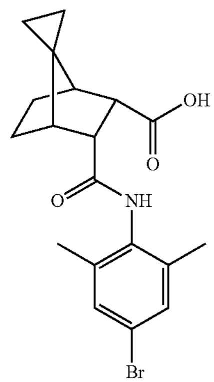 [SMILES: Cc1cc(Br)cc(C)c1NC(=O)C1C(C(=O)O)C2CCC1C21CC1] | 2124 (0.67) | NA |
| 74 | 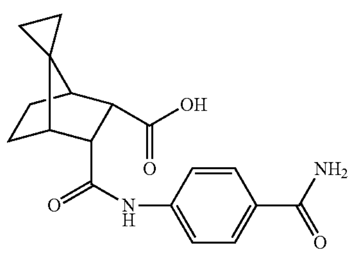 [SMILES: NC(=O)c1ccc(NC(=O)C2C(C(=O)O)C3CCC2C32CC2)cc1] | 2772 (0.67) | NA |
| 75 | 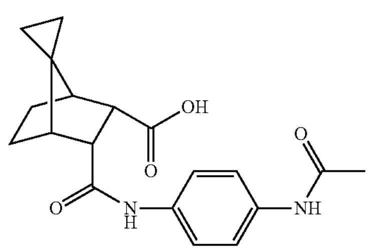 [SMILES: CC(=O)Nc1ccc(NC(=O)C2C(C(=O)O)C3CCC2C32CC2)cc1] | NA | NA |
| 76 | 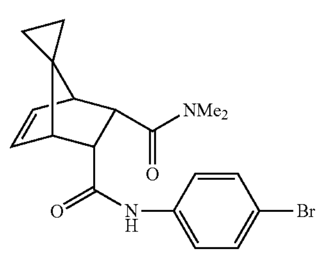 [SMILES: CN(C)C(=O)C1C(C(=O)Nc2ccc(Br)cc2)C2C=CC1C21CC1] | 3719 (0.5) | ND |

TABLE 1-continued

| Compound Number | Structure | FPRL1 EC$_{50}$ (rel. eff.) | FPR1 EC$_{50}$ (rel. eff.) |
|---|---|---|---|
| 77 | 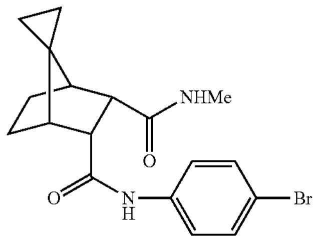 [SMILES: CNC(=O)C1C(C(=O)Nc2ccc(Br)cc2)C2CCC1C21CC1] | 9.7 (0.95) | NA |
| 78 | 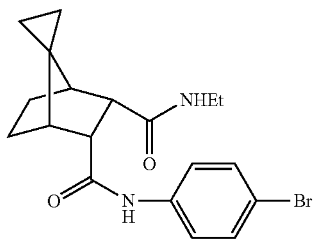 | 12.5 (0.95) | NA |
| 79 | 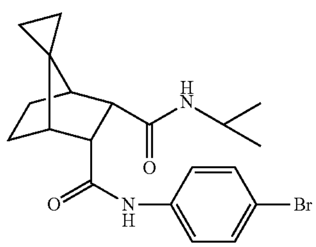 [SMILES: CC(C)NC(=O)C1C(C(=O)Nc2ccc(Br)cc2)C2CCC1C21CC1] | 6.6 (1.0) | NA |
| 80 | 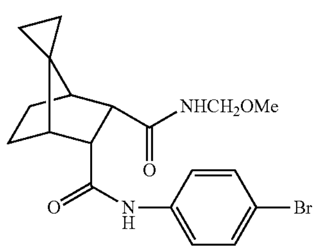 | 55.9 (0.97) | NA |
| 81 | 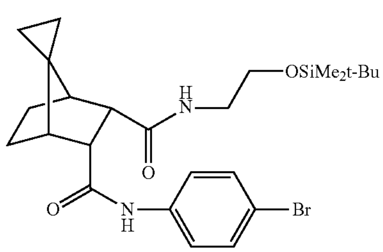 | NT | NT |
| 82 | 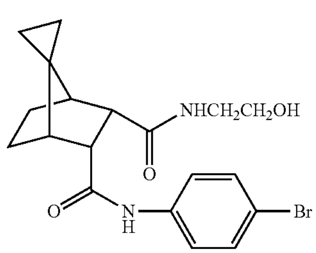 | 8.8 (0.86) | NA |

TABLE 1-continued
| Compound Number | Structure | FPRL1 EC$_{50}$ (rel. eff.) | FPR1 EC$_{50}$ (rel. eff.) |
|---|---|---|---|
| 83 | 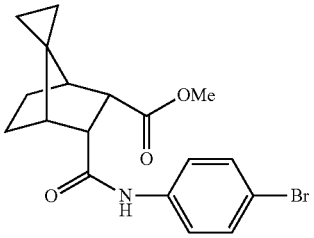 [SMILES: COC(=O)C1C(C(=O)Nc2ccc(Br)cc2)C2CCC1C21CC1] | 1683 (0.68) | NT |
| 84 | 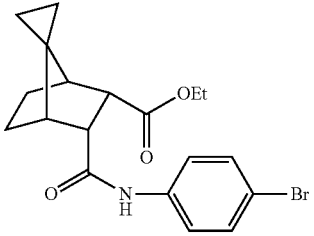 [SMILES: CCOC(=O)C1C(C(=O)Nc2ccc(Br)cc2)C2CCC1C21CC1] | 1373 (0.74) | NT |
| 85 | 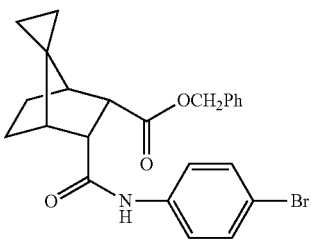 | 2140 (0.88) | NA |
| 86 | 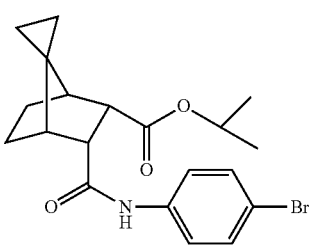 [SMILES: CC(C)OC(=O)C1C(C(=O)Nc2ccc(Br)cc2)C2CCC1C21CC1] | 2106 (1.0) | NA |
| 87 | 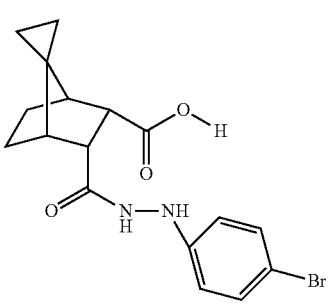 [SMILES: O=C(O)C1C(C(=O)NNc2ccc(Br)cc2)C2CCC1C21CC1] | 456 (0.89) | NA |
| 88 | 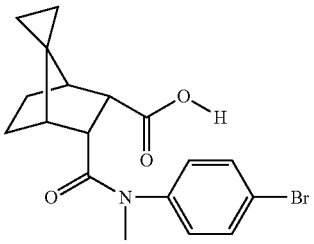 [SMILES: CN(C(=O)C1C(C(=O)O)C2CCC1C21CC1)c1ccc(Br)cc1] | 410 (0.94) | NA |

TABLE 1-continued

| Compound Number | Structure | FPRL1 EC$_{50}$ (rel. eff.) | FPR1 EC$_{50}$ (rel. eff.) |
|---|---|---|---|
| 89 | 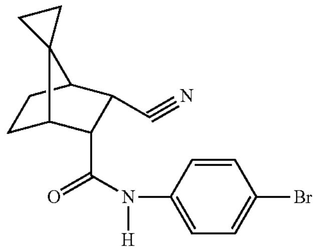 [SMILES: N#CC1C(C(=O)Nc2ccc(Br)cc2)C2CCC1C21CC1] | 1087 (0.82) | NA |
| 90 | 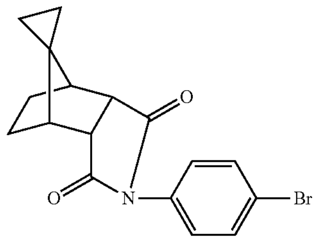 [SMILES: O=C1C2C(C(=O)N1c1ccc(Br)cc1)C1CCC2C12CC2] | 6557 (0.38) | ND |
| 91 | 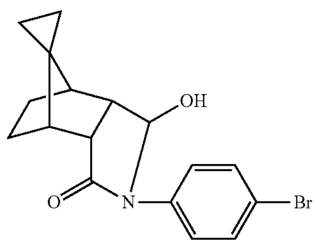 [SMILES: O=C1C2C(C(O)N1c1ccc(Br)cc1)C1CCC2C12CC2] | NA | NA |
| 92 | 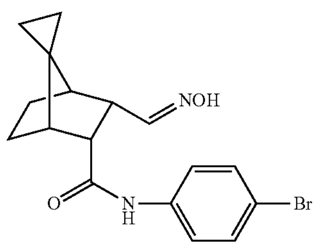 | 4383 (0.5) | NA |
| 93 | 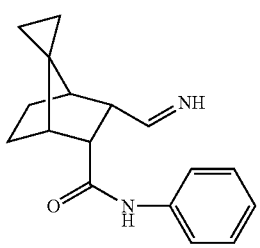 [SMILES: N=CC1C(C(=O)Nc2ccccc2)C2CCC1C21CC1] | 5811 (0.58) | NA |
| 94 | 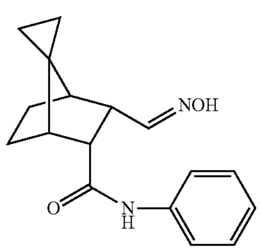 | 2833 (0.49) | NA |

NA = Not Active (EC50 > 10 μM),
ND = Not Determined

The compounds and methods of the invention are useful in treating disorders associated with agonism or antagonism of FPRL-1 receptors. As such, the compounds and methods of the invention are useful for treating disorders such, for example, wet and dry age-related macular degeneration (ARMD), diabetic retinopathy (proliferative), retinopathy of prematurity (ROP), diabetic macular edema, uveitis, retinal vein occlusion, cystoid macular edema, glaucoma, branch vein occlusion, Best's vitelliform macular degeneration, retinitis pigmentosa, proliferative vitreoretinopathy (PVR), or any other degenerative disease of either the photoreceptors or the RPE.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The following examples are intended only to illustrate the invention and should in no way be construed as limiting the invention.

EXAMPLES

Compound 1

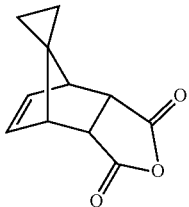

Spiro[bicyclo[2.2.1]hept[2]ene-7,1'-cyclopropane]-5,6-dicarboxylic Acid Anhydride (Compound 1)

To a solution of maleic anhydride (0.20 g, 2.0 mmol) in chloroform (5.0 mL) at 0° C. under Argon atmosphere was added dropwise spiro[2,4]hepta-4,6-diene (0.20 mL, 2.0 mmol), and the reaction was allowed to warm up slowly to ambient temperature and stirred for 18 h in the dark. The solvent was then removed, and the residue was recrystallized from methanol to afford the title compound as a white solid $^1$HNMR (300 MHz, CDCl$_3$): δ ppm 0.40-0.52 (m, 2H), 0.53-0.61 (m, 2H), 2.81 (ddd, J=4.47, 2.12, 1.90 Hz, 2H), 3.66 (dd, J=2.93, 1.47 Hz, 2H), 6.30 (t, J=1.90 Hz, 2H).

Compound 2

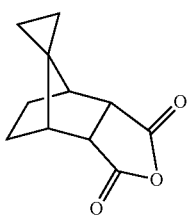

Spiro[bicyclo[2.2.1]heptane-7,1'-cyclopropane]-2,3-dicarboxylic Acid Anhydride (Compound 2)

A mixture of Compound 1 (0.10 g, 0.53 mmol) and a catalytic amount of 10% Pd—C in 1,4-dioxane (5.0 mL) was stirred under a hydrogen atmosphere for 18 h, and then the solution was filtered through Celite. The solvent was removed under vacuum, and the residue was recrystallized from methanol to produce the title compound as a white solid.

$^1$HNMR (300 MHz, CDCl$_3$): δ ppm 0.63 (s, 4H), 1.53 (d, J=8.50 Hz, 2H), 1.90 (d, J=1.76 Hz, 2H), 2.0-2.09 (m, 2H), 3.57 (d, J=1.76 Hz, 2H).

Compound 3

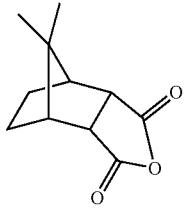

7,7-Dimethylbicyclo[2.2.1]heptane-2,3-dicarboxylic Acid Anhydride (Compound 3)

A flask containing a mixture of Compound 1 (0.1562 g, 0.82 mmol) and PtO$_2$ (catalytic amount) in glacial acetic acid was evacuated and filled with dry nitrogen three times. The resulting suspension was stirred at 60° C. under a hydrogen atmosphere for 18 h. The reaction was cooled to room temperature, and the solution was filtered through Celite with the aid of glacial acetic acid. The solvent was removed under reduced pressure, and the residue was recrystallized in MeOH/H$_2$O to afford the title compound as a white solid.

$^1$HNMR (300 MHz, CDCl$_3$): δ ppm 1.08 (s, 6H), 1.37 (s, 1H), 1.40 (s, 1H), 1.90 (d, J=2.05 Hz, 1H), 1.93 (d, J=1.47 Hz, 1H), 2.11-2.20 (m, 2H), 3.52-3.60 (m, 2H).

Compound 4

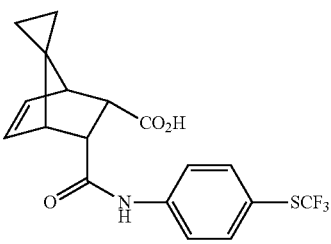

(+/−)-(1S,4R,5S,6R)-6-(4-(Trifluoromethylthio)phenylcarbamoyl)Spiro[bicyclo[2.2.1]hept[2]ene-7,1'-cyclopropane]-5-carboxylic Acid (Compound 4)

General Procedure A

To a solution of Compound 1 (95 mg, 0.5 mmol) in CHCl$_3$ (3 mL) was added 4-trifluoromethylthioaniline (96 mg, 0.5 mmol) in CHCl$_3$ (1 mL). The mixture was stirred for 16 h at ambient temperature. The resulting precipitate was filtered and washed with cold (0° C.) CHCl$_3$ (3 mL) to give the title compound as a white solid.

$^1$HNMR (300 MHz, CD$_3$OD): δ 0.42-0.60 (m, 4H), 2.45-2.55 (m, 2H), 3.71 (dq, J=3.3, 9.9 Hz, 2H), 6.22-6.38 (m, 2H), 7.53-7.68 (m, 4H).

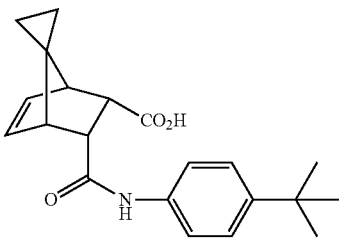

Compound 5

(+/−)-(1R,4S,5R,6S)-5-(4-tert-Butylphenylcarbamoyl)spiro[bicyclo[2.2.1]hept[2]ene-7,1'-cyclopropane]-6-carboxylic Acid (Compound 5)

Following General Procedure A, Compound 1 (39 mg, 0.2 mmol) and 4-t-butyl aniline (29 mg, 0.2 mmol) in THF (2 mL) were converted into the title compound, which was isolated as a white solid.

$^1$HNMR (300 MHz, $CD_3COCD_3$): δ 0.44-0.58 (m, 4H), 1.27 (s, 9H), 2.53 (d, J=9.5 Hz, 2H), 3.43 (dd, J=3.0, 9.9 Hz, 1H), 3.61 (dd, J=3.0, 9.9 Hz, 1H), 6.22 (d, J=3.0 Hz, 1H), 6.32 (d, J=3.0 Hz, 1H), 7.28 (dd, J=2.1, 6.6 Hz, 2H), 7.50 (dd, J=2.1, 6.6 Hz, 2H).

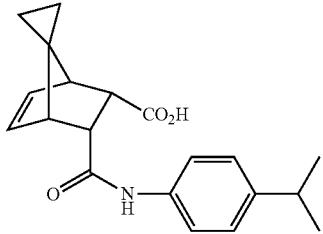

Compound 6

(+/−)-(1S,4R,5S,6R)-6-(4-Isopropylphenylcarbamoyl)spiro[bicyclo[2.2.1]hept[2]ene-7,1'-cyclopropane]-5-carboxylic Acid (Compound 6)

Following General Procedure A, Compound 1 (41 mg, 0.22 mmol) and 4-isopropyl aniline (45 mg, 0.33 mmol) in THF (3 mL) were converted into the title compound, which was isolated as a white solid after purification by silica gel chromatography.

$^1$HNMR (300 MHz, $CD_3COCD_3$): δ 0.42-0.55 (m, 4H), 1.20 (d, J=6.9 Hz, 6H), 2.49 (s, 1H), 2.55 (s, 1H), 2.84 (sept, J=6.9 Hz, 1H), 3.43 (dd, J=3.3, 10.2 Hz, 1H), 3.61 (dd, J=3.3, 10.2 Hz, 1H), 6.20 (d, J=3.0 Hz, 1H), 6.32 (d, J=3.0 Hz, 1H), 7.12 (dd, J=1.8, 6.6 Hz, 2H), 7.50 (dd, J=1.8, 6.6 Hz, 2H).

Compound 7

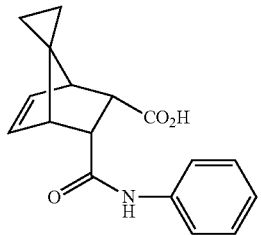

(+/−)-(1S,4R,5S,6R)-6-(Phenylcarbamoyl)spiro[bicycle[2.2.1]hept[2]ene-7,1'cyclopropane]-5-carboxylic Acid (Compound 7)

Following General Procedure A, Compound 1 (36 mg, 0.18 mmol) and aniline (24 mg, 0.26 mmol) in $CHCl_3$ (2 mL) were converted into the title compound, which was isolated as a white solid.

$^1$HNMR (300 MHz, $CD_3OD$): δ 0.42-0.60 (m, 4H), 2.49 (d, J=3.0 Hz, 2H), 3.48 (dd, J=3.0, 12.0 Hz, 1H), 3.59 (dd, J=3.0, 9.0 Hz, 1H), 6.24 (dd, J=3.0, 6.0 Hz, 1H), 6.37 (dd, J=3.0, 6.0 Hz, 1H), 7.03 (2, J=6.0 Hz, 2H), 7.25 (t, J=6.0 Hz, 2H), 7.47 (d, J=6.0 Hz, 1H).

Compound 8

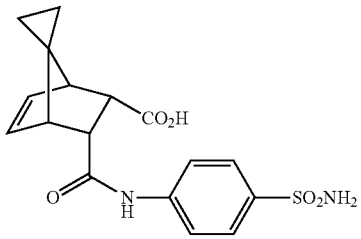

(+/−)-(1S,4R,5S,6R)-6-(4-Sulfamoylphenylcarbamoyl)spiro[bicyclo[2.2.1]hept[2]ene-7,1'-cyclopropane]-5-carboxylic Acid (Compound 8)

Following General Procedure A, Compound 1 (28 mg, 0.15 mmol) in $CHCl_3$ (2 mL) and 4-aminobenzenesulfonamide (26 mg, 0.15 mmol) in MeOH (2 mL) were mixed together at ambient temperature for 16 h to produce the title compound, which was isolated as a white solid.

$^1$HNMR (300 MHz, $CD_3CN$): δ 0.42-0.60 (m, 4H), 2.57 (d, J=9.0 Hz, 2H), 3.49 (dd, J=3.0, 12.0 Hz, 1H), 3.55 (dd, J=3.0, 9.0 Hz, 1H), 6.27 (dd, J=3.0, 6.0 Hz, 1H), 6.33 (dd, J=3.0, 6.0 Hz, 1H), 7.68 (d, J=9.0 Hz, 2H), 7.79 (t, J=6.0 Hz, 2H).

Compound 9

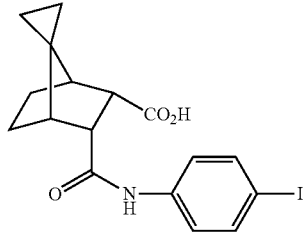

(+/−)-(1R,2S,3R,4S)-3-(4-Iodophenylcarbamoyl)spiro[bicyclo[2.2.1]heptane-7,1'-cyclopropane]-2-carboxylic Acid (Compound 9)

Following General Procedure A, Compound 2 (0.084 g, 0.44 mmol) and 4-iodoaniline (0.090 g, 0.44 mmol) in chloroform (6 mL) were converted into the title compound, which was isolated as a white solid.

$^1$HNMR (300 MHz, acetone-$d_6$): δ ppm 0.45-0.71 (m, 4H), 1.66 (d, J=18.46 Hz, 4H), 1.78-1.93 (m, 1H), 2.18-2.34 (m, 1H), 3.17 (dd, J=8.08, 1.90 Hz, 1H), 3.45 (dd, J=11.43, 4.40 Hz, 1H), 7.43-7.54 (m, 2H), 7.55-7.67 (m, 2H), 9.21 (br. s., 1H).

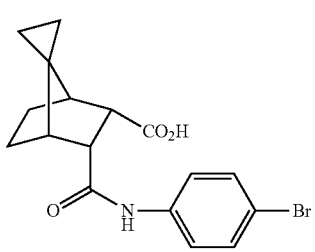

Compound 10

(+/−)-(1R,2S,3R,4S)-3-(4-Bromophenylcarbamoyl)
spiro[bicyclo[2.2.1]heptane-7,1'-cyclopropane]-2-
carboxylic Acid (Compound 10)

Following General Procedure A, Compound 2 (0.090 g, 0.47 mmol) and 4-bromoaniline (0.080 g, 0.47 mmol) in chloroform (3.0 mL) were converted into the title compound, which was isolated as a white solid.

$^1$HNMR (300 MHz, acetone-$d_6$): δ ppm 0.45-0.70 (m, 4H), 1.53-1.76 (m, 4H), 1.76-1.93 (m, 1H), 2.18-2.36 (m, 1H), 3.15 (ddd, J=11.43, 3.52, 1.76 Hz, 1H), 3.46 (dd, J=11.43, 3.52 Hz, 1H), 7.42 (d, J=5.08 Hz, 2H), 7.62 (d, J=9.08 Hz, 2H), 9.23 (br. s., 1H).

Racemic Compound 10 was Separated into Individual Enantiomers 10A and 10B by Chiral Chromatography Absolute Stereochemistry Determined by X-ray Crystallography)

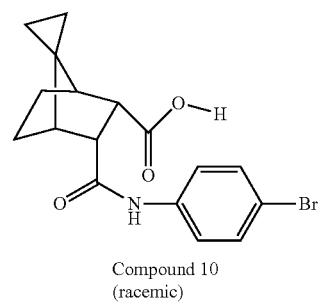

Compound 10
(racemic)

| Chiral chromatography

[α] = −39.0°
c = 1.09, MeOH
Compound 10A

[α] = +36.0°
c = 1.14, MeOH
Compound 10B

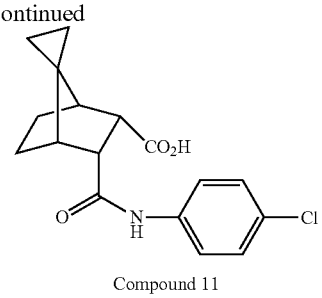

Compound 11

(+/−)-(1R,2S,3R,4S)-3-(4-Chlorophenylcarbamoyl)
spiro[bicyclo[2.2.1]heptane-7,1'-cyclopropane]-2-
carboxylic Acid (Compound 11)

Following General Procedure A, Compound 2 (0.042 g, 0.22 mmol) and 4-chloroaniline (0.028 g, 0.22 mmol) in chloroform (1.5 mL) were converted into the title compound, which was isolated as a white solid.

$^1$HNMR (300 MHz, acetone-$d_6$): δ ppm 0.42-0.66 (m, 4H), 1.51-1.75 (m, 4H), 1.78-1.91 (m, 1H), 2.20-2.35 (m, 1H), 3.15 (ddd, J=11.43, 3.66, 1.90 Hz, 1H), 3.46 (ddd, J=11.43, 4.69, 1.17 Hz, 1H), 7.28 (d, J=5.27 Hz, 2H), 7.66 (d, J=5.27 Hz, 2H), 9.22 (br. s., 1H), 10.31 (br. s., 1H).

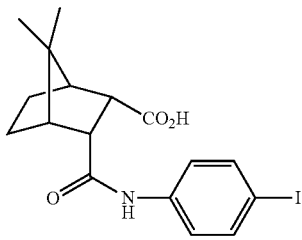

Compound 12

(+/−)-(1R,2S,3R,4S)-3-(4-Iodophenylcarbamoyl)-7,
7-dimethylbicyclo[2.2.1]heptane-2-carboxylic Acid
(Compound 12)

Following General Procedure A, Compound 3 (0.019 g, 0.10 mmol) and 4-iodoaniline (0.020 g, 0.10 mmol) in chloroform (2 mL) were converted into the title compound, which was isolated as a white solid.

$^1$HNMR (300 MHz, acetone-$d_6$) δ ppm 1.08 (s, 3H), 1.15 (s, 3H), 1.53-1.70 (m, 2H), 1.81 (t, J=3.37 Hz, 2H), 1.95 (t, J=8.96 Hz, 1H), 2.23 (dd, J=8.94, 7.47 Hz, 1H), 3.17 (ddd, J=11.57, 3.66, 2.05 Hz, 1H), 3.49 (ddd, J=11.65, 4.47, 1.47 Hz, 1H), 7.43-7.54 (m, 2H), 7.57-7.66 (m, 2H), 9.23 (br. s., 1H)

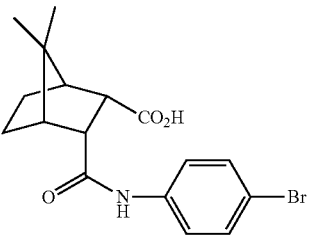

Compound 13

(+/−)-(1R,2S,3R,4S)-3-(4-Bromophenylcarbamoyl)-7,7-dimethylbicyclo[2.2.1]heptane-2-carboxylic Acid (Compound 13)

Following General Procedure A, Compound 3 (0.047 g, 0.24 mmol) and 4-bromoaniline (0.041 g, 0.24 mmol) in chloroform (4 mL) were converted into the title compound, which was isolated as a white solid.

$^1$HNMR (300 MHz, acetone-$d_6$): δ ppm 0.92-0.23 (m, 6H), 1.50-1.88 (m, 4H), 1.95 (br. s., 1H), 2.22 (br. s., 1H), 3.19 (br. s., 1H), 3.48 (br. s., 1H), 7.42 (d, J=7.33 Hz, 2H), 7.61 (d, J=7.91 Hz, 2H), 9.25 (br. s., 1H)

Compound 14

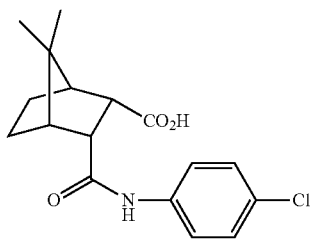

(+/−)-(1R,2S,3R,4S)-3-(4-Chlorophenylcarbamoyl)-7,7-dimethylbicyclo[2.2.1]heptane-2-carboxylic Acid (Compound 14)

Following General Procedure A, Compound 3 (0.047 g, 0.24 mmol) and 4-chloroaniline (31 mg, 0.24 mmol) in chloroform (4 mL) was converted into the title compound, which was isolated as a white solid.

$^1$HNMR (300 MHz, acetone-$d_6$): δ ppm 1.08 (br. s., 3H), 1.16 (br. s., 3H), 1.52-1.87 (m, 4H), 1.9 (br. s., 1H), 2.23 (br. s., 1H), 3.19 (br. s., 1H), 3.48 (br. s., 1H), 7.28 (d, J=8.20 Hz, 2H), 7.66 (d, J=8.20 Hz, 2H), 9.26 (br. s., 1H).

Compound 15

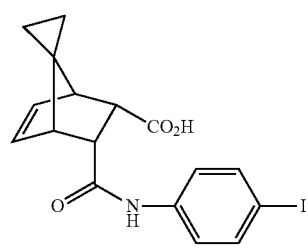

(+/−)-(1S,4R,5S,6R)-6-(4-Iodophenylcarbamoyl)spiro[bicyclo[2.2.1]hept[2]ene-7,1'-cyclopropane]-5-carboxylic Acid (Compound 15)

Following General Procedure A, Compound 1 (0.20 g, 1.05 mmol) and 4-iodoaniline (229 mg, 1.05 mmol) in chloroform (25 mL) were mixed together at ambient temperature for 16 h to produce the title compound, which was isolated as a white solid.

$^1$HNMR (300 MHz, acetone-$d_6$): δ ppm 0.34-0.57 (m, 4H), 2.42-2.61 (m, 2H), 3.37-3.50 (m, 1H), 3.53-3.65 (m, 1H), 6.14-6.26 (m, 1H), 6.31 (dd, J=6.01, 2.49 Hz, 1H), 7.44 (q, J=4.79 Hz, 2H), 7.53-7.65 (m, 2H), 9.16 (br. s., 1H), 10.37 (br. s., 1H).

Compound 16

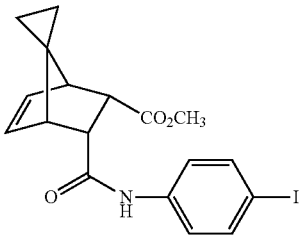

Methyl(+/−)-(1S,4R,5S,6R)-6-(4-Iodophenylcarbamoyl)spiro[bicyclo[2.2.1]hept[2]ene-7,1'-cyclopropane]-5-carboxylate (Compound 16). General Procedure B A mixture of Compound 15 (0.020 g, 0.049 mmol), methyl iodide (6.0 μL, 0.098 mmol), and sodium bicarbonate (0.02 g, 0.245 mmol) in DMF (2.0 mL) was stirred at ambient temperature for 18 h. The solution was filtered and the solvent was removed in vacuo. The residue was purified by preparative TLC using ethyl acetate (30%) and hexane (70%) as eluent to afford the title compound as a white solid.

$^1$HNMR (300 MHz, CDCl$_3$): δ ppm 0.39-0.54 (m, 2H), 0.59 (d, J=7.03 Hz, 2H), 2.58 (br. s., 2H), 3.51 (d, J=1.47 Hz, 2H), 3.55 (s, 3H), 6.35 dt, J=2.98, 1.47 Hz, 1H) 6.62 (dt, J=2.93, 1.47 Hz, 1H), 7.21-7.27 (d, J=8.79 Hz, 2H), 7.32 (br. s., 1H), 7.58 (d, J=8.79 Hz, 2H).

Compound 17

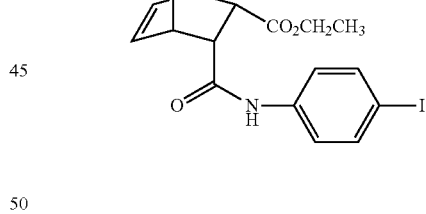

Ethyl(+/−)-(1S,4R,5S,6R)-6-(4-Iodophenylcarbamoyl)spiro[bicyclo[2.2.1]hept[2]ene-7,1'-cyclopropane]-5-carboxylate (Compound 17)

Following General Procedure B, Compound 15 (0.031 g, 0.076 mmol) and ethyl iodide (12.2 μL, 0.152 mmol) were converted into the title compound, which was isolated as a white solid.

$^1$HNMR (300 MHz, CDCl$_3$): δ ppm 0.37-0.51 (m, 2H), 0.57 (d, J=7.03 Hz, 2H), 1.08 (t, J=7.18 Hz, 3H), 2.58 (br. s., 2H), 3.51 (d, J=1.76 Hz, 2H), 3.99 (m, 2H), 6.36 (dd, J=3.37, 2.20 Hz, 1H), 6.61 (dd, J=3.52, 2.34 Hz, 1H), 7.19-7.31 (m, 2H), 7.38 (s, 1H), 7.57 (d, 2H).

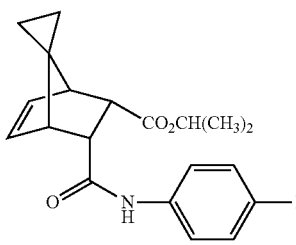

Compound 18

Iso-propyl(+/−)-(1S,4R,5S,6R)-6-(4-Iodophenylcarbamoyl)spiro[bicyclo[2.2.1]hept[2]ene-7,1'-cyclopropane]-5-carboxylate (Compound 18)

Following General Procedure B, Compound 15 (0.045 g, 0.11 mmol) and 2-iodopropane (22.0 μL, 0.22 mmol) were converted into the title compound, which was isolated as a white solid.

¹HNMR (300 MHz, CDCl₃): δ ppm 0.37-0.51 (m, 2H), 0.57 (d, J=7.03 Hz, 2H), 1.08 (t, J=7.18 Hz, 3H), 2.58 (br. s., 2H), 3.51 (d, J=1.76 Hz, 2H), 3.99 (m, 2H), 6.36 (dd, J=3.37, 2.20 Hz, 1H), 6.61 (dd, J=3.52, 2.34 Hz, 1H), 7.19-7.31 (m, 2H), 7.38 (s, 1H), 7.57 (d, 2H).

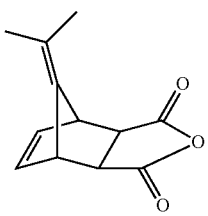

Compound 19-exo

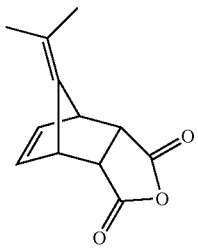

Compound 19-endo (1R,4S,5S,6R)-7-(Propan-2-ylidene)bicyclo[2.2.1]hept[2]ene-5,6-dicarboxylic Acid Anhydride (Compound 19-exo) and (1R,4S,5R,6S)-7-(Propan-2-ylidene)bicyclo[2.2.1]hept[2]ene-5,6-dicarboxylic Acid Anhydride (Compound 19-endo)

To a cold (0° C.) mixture of ether (40 mL) and maleic anhydride (4.4 g, 44.9 mmol) was added dimethylfulvene (4.4 g, 41.51 mmol). The solution was stirred for 8 h at 0° C. A solid separated, which was recrystallized from diethyl ether to obtain the pure exo product (Compound 19-exo). The eluent, which contained a mixture of endo and exo isomers, was concentrated to dryness in vacuo. The residue was purified, and the isomers were separated, by silica gel chromatography (hexane:ethyl acetate::4:1) to produce the endo isomer (Compound 19-endo) as a white solid.

Compound 19-exo: ¹HNMR (300 MHz, CDCl₃): δ 1.59 (s, 6H), 3.04 (s, 2H), 3.87 (t, J=3.0 Hz, 2H), 6.45 (t, J=3.0 Hz, 2H).

Compound 19-endo: ¹HNMR (300 MHz, CDCl₃): δ 1.58 (s, 6H), 3.52 (dd, J=3.0, 4.5 Hz, 2H), 3.92 (dd, J=3.0, 4.6 Hz, 2H), 6.44 (t, J=3.0 Hz, 2H).

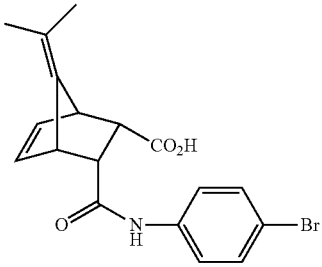

Compound 20

(+/−)-(1S,4R,5S,6R)-6-(4-Bromophenylcarbamoyl)[bicyclo[2.2.1]hept[2]ene-7-propan-2-ylidene]-5-carboxylic Acid (Compound 20)

Following General Procedure A, Compound 19-endo (0.114 g, 0.56 mmol) and 4-bromoaniline (96.3 mg, 0.56 mmol) in THF (4 mL) were mixed together at ambient temperature for 16 h to produce the title compound, which was isolated as a white solid.

¹HNMR (300 MHz, CDCl₃): δ 1.59 (s, 3H), 1.60 (s, 3H), 3.23 (dd, J=3.0, 9.0 Hz, 1H), 3.29 (dd, J=3.0, 9.0 Hz, 1H), 3.61 (br s, 1H), 3.67 (br s, 1H), 6.25 (dd, J=3.0, 6.0 Hz, 1H), 6.39 (dd, J=3.0, 6.0 Hz, 1H), 7.45 (d, J=3.0 Hz, 4H).

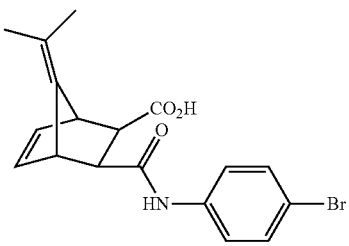

Compound 21

(+/−)-(1S,4R,5R,6S)-6-(4-Bromophenylcarbamoyl)[bicyclo[2.2.1]hept[2]ene-7-propan-2-ylidene]-5-carboxylic Acid (Compound 21)

Following General Procedure A, Compound 19-exo (0.068 g, 0.35 mmol) and 4-bromoaniline (60.2 mg, 0.35 mmol) in THF (2 mL) were mixed together at ambient temperature for 16 h to produce the title compound, which was isolated as a white solid after recrystallization from acetonitrile.

¹HNMR (300 MHz, CD₃OD): δ 1.61 (s, 3H), 1.70 (s, 3H), 2.64 (d, J=9.9 Hz, 1H), 2.76 (d, J=9.9 Hz, 1H), 3.47 (br s, 1H), 3.61 (br s, 1H), 6.39 (t, J=2.1 Hz, 2H), 7.40 (s, 4H).

Compound 22

(+/−)-(1S,4R,5S,6R)-6-(4-Iodophenylcarbamoyl)
[bicyclo[2.2.1]hept[2]ene-7-propan-2-ylidene]-5-
carboxylic Acid (Compound 22)

Following General Procedure A, Compound 19-endo (86 mg, 0.42 mmol) and 4-iodo-aniline (92 mg, 0.42 mmol) in THF (3 mL) were mixed together at ambient temperature for 16 h to produce the title compound, which was isolated as a white solid.

$^1$HNMR (300 MHz, CD$_3$OD): δ 1.59 (s, 3H), 1.60 (s, 3H), 3.30 (dd, J=3.0, 9.0 Hz, 2H), 3.60 (m, 2H), 6.27 (dd, J=3.0, 6.0 Hz, 1H), 6.39 (dd, J=3.0, 6.0 Hz, 1H), 7.31 (d, J=9.0 Hz, 2H), 7.57 (d, J=9.0 Hz, 2H).

Compound 23

(1R,2R,3S,4S)-7-(Propan-2-ylidene)bicyclo[2.2.1]
heptane-2,3-dicarboxylic Acid Anhydride (Compound 23)

To a solution of Compound 19-exo (300 mg, 1.6 mmol) in EtOAC (10 mL) was added 10% Pd—C (16 mg) under argon. The flask was evacuated and refilled with hydrogen gas from a balloon, and the reaction was stirred for 2 h. The reaction was diluted with ethyl acetate (20 mL) and hexane (20 mL), and filtered through a short column of Celite. The product (Compound 23) was collected as white solid after removing the solvent under vacuum.

$^1$HNMR (300 MHz, CDCl$_3$): δ 1.42-1.52 (m, 2H), 1.66 (s, 6H), 1.70-1.80 (m, 2H), 2.69 (s, 2H), 3.20 (t, J=2.4 Hz, 2H).

Compound 24

(+/−)-(1S,2R,3S,4S)-3-(4-Bromophenylcarbamoyl)
[bicyclo[2.2.1]heptane-7-propan-2-ylidene]-2-carboxylic Acid (Compound 24)

Following General Procedure A, Compound 23 (100 mg, 0.49 mmol) and 4-bromoaniline (89 mg, 0.51 mmol) in THF (4 mL) were mixed together at ambient temperature for 16 h to produce the title compound, which was isolated as a white solid.

$^1$HNMR (300 MHz, CDCl$_3$): δ 1.42-1.52 (m, 2H), 1.66 (s, 6H), 1.70-1.80 (m, 2H), 2.69 (s, 2H), 3.20 (t, J=2.4 Hz, 2H).

Compound 25

(+/−)-(1S,4R,5S,6R)-6-(5-Bromo-2-pyridylcarbamoyl)spiro[bicyclo[2.2.1]hept[2]ene-7,1'-cyclopropane]-5-carboxylic Acid (Compound 25)

Compound 1 (41 mg, 0.22 mmol) and 2-amino-5-bromopyridine (46 mg, 0.27 mmol) in THF (3.0 mL) were heated in an oil bath at 70° C. for 24 h to produce the title compound, which was isolated as a white solid.

$^1$HNMR (300 MHz, CD$_3$SOCD$_3$): δ 0.40-0.48 (m, 4H), 2.40-2.49 (m, 1H), 3.30 (d, J=6.0 Hz, 1H), 3.38 (d, J=12.0 Hz, 1H), 3.60 (d, J=12.0 Hz, 1H), 6.16 (d, J=6.0 Hz, 1H), 6.21 (d, J=6.0 Hz, 1H), 7.92 (d, J=9.0 Hz, 1H), 7.97 (d, J=9.0 Hz, 1H), 8.38 (brs, 1H).

Additional Compounds that were Prepared by General Procedure A

Compound 26

(+/−)-(1R,4S,5R,6S)-5-([1,1'-Biphenyl]-4-ylcarbamoyl)spiro[bicyclo[2.2.1]hept[2]ene-7,1'-cyclopropane]-6-carboxylic Acid (Compound 26)

$^1$HNMR (300 MHz, CD$_3$CN): δ 0.44-0.60 (m, 4H), 2.58 (d, J=12.0 Hz, 2H), 3.48 (dd, J=3.3, 10.2 Hz, 1H), 3.56 (dd, J=3.3, 10.2 Hz, 1H), 6.26 (dd, J=3.0, 5.7 Hz, 1H), 6.37 (dd, J=3.0, 5.7 Hz, 1H), 7.35 (t, J=8.4 Hz, 1H), 7.46 (t, J=8.4 Hz, 2H), 7.58-7.68 (m, 6H).

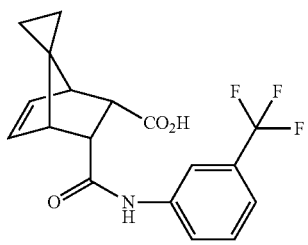

Compound 27

(+/−)-(1S,4R,5S,6R)-6-β3-(Trifluoromethyl)phenyl)
carbamoyl)spiro[bicyclo-[2.2.1]hept[2]ene-7,1'-cyclopropane]-5-carboxylic Acid (Compound 27)

$^1$HNMR (300 MHz, acetone-$d_6$): δ 0.33-0.66 (m, 4H), 2.52 (br.s., 1H), 2.58 (br.s., 1H), 3.48 (dd, J=9.96, 3.52 Hz, 1H), 3.63 (dd, J=9.96, 3.52 Hz, 1H), 6.17-6.29 (m, 1H), 6.29-6.37 (m, 1H), 7.32 (d, J=7.62 Hz, 1H), 7.47 (t, J=7.91 Hz, 1H), 7.72. (d, J=7.91 Hz, 1H), 8.13 (s, 1H), 9.38 (br.s., 1H).

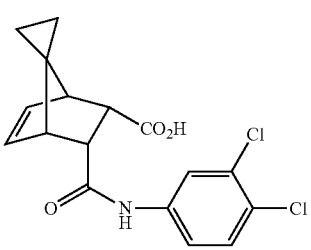

Compound 28

(+/−)-(1S,4R,5S,6R)-6-((3,4-Dichlorophenyl)carbamoyl)spiro[bicyclo[2.2.1]hept[2]-ene-7,1'-cyclopropane]-5-carboxylic Acid (Compound 28)

$^1$HNMR (300 MHz, acetone-$d_6$): δ 0.47 (br.s., 4H), 2.51 (d, J=11.13 Hz, 2H), 3.46 (br.s., 1H), 3.55 (br.s., 1H), 6.25 (d, J=12.60 Hz, 2H), 7.38 (br.s., 2H), 7.98 (br.s., 1H), 9.31 (br.s., 1H).

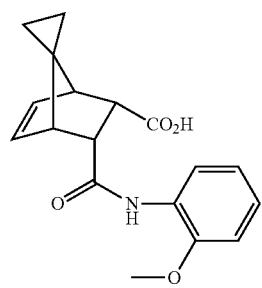

Compound 29

(+/−)-(1S,4R,5S,6R)-6-((2-Methoxyphenyl)carbamoyl)spiro[bicyclo[2.2.1]hept[2]ene-7,1'-cyclopropane]-5-carboxylic Acid (Compound 29)

$^1$HNMR (300 MHz, acetone-$d_6$): δ 0.41-0.56 (m, 4H), 2.51 (br.s., 1H), 2.58 (br.s., 1H), 3.41-3.57 (m, 1H), 3.73 (dd, J=10.11, 3.37 Hz, 1H), 3.86 (s, 3H), 6.25 (dd, J=5.57, 2.93 Hz, 1H), 6.40 (dd, J=5.57, 2.64 Hz, 1H), 6.77-6.91 (m, 1H), 6.92-7.01 (m, 2H), 8.24 (d, J=8.20 Hz, 1H), 8.42 (br.s., 1H).

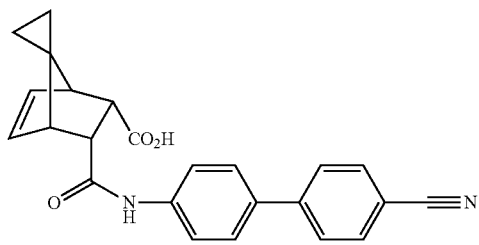

Compound 30

(+/−)-(1S,4R,5S,6R)-6-((4'-Cyano-[1,1'-biphenyl]-4-yl)carbamoyl)spiro[bicyclo-[2.2.1]hept[2]ene-7,1'-cyclopropane]-5-carboxylic Acid (Compound 30)

$^1$HNMR (300 MHz, $CD_3CN$): δ 0.45-0.60 (m, 4H), 2.57 (d, J=11.7 Hz, 2H), 3.49 (dd, J=3.0, 6.0 Hz, 1H), 3.56 (dd, J=3.0, 6.0 Hz, 1H), 6.25 (d, J=6.0 Hz, 1H), 6.35 (d, J=6.0 Hz, 1H), 7.64 (s, 4H), 7.79 (s, 4H).

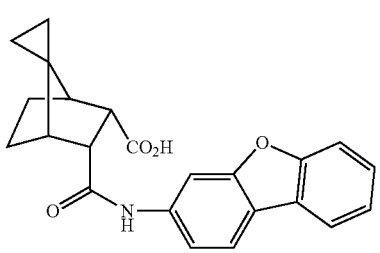

Compound 31

(+/−)-(1S,4R,5S,6R)-6-(dibenzo[b,d]furan-3-ylcarbamoyl)spiro[bicyclo[2.2.1]-heptane-7,1'-cyclopropane]-5-carboxylic acid (Compound 31)

$^1$HNMR (300 MHz, $CD_3SOCD_3$): δ 0.45-0.62 (m, 4H), 1.50-1.65 (m, 2H), 1.70-1.82 (m, 2H), 2.05-2.20 (m, 1H), 3.05 (d, J=11.4 Hz, 1H), 3.28 (d, J=6.9 Hz, 1H), 3.39 (dd, J=4.8, 11.4 Hz, 1H), 7.34 (t, J=7.5 Hz, 1H), 7.43 (t, J=7.5 Hz, 2H), 7.64 (d, J=8.1 Hz, 1H), 8.00 (t, J=8.1 Hz, 2H), 8.10 (s, 1H).

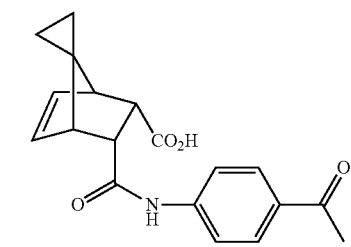

Compound 32

(+/−)-(1R,4S,5R,6S)-5-((4-Acetylphenyl)carbamoyl)spiro[bicyclo[2.2.1]hept[2]ene-7,1'-cyclopropane]-6-carboxylic Acid (Compound 32)

$^1$HNMR (300 MHz, acetone-$d_6$): δ 0.51 (br.s., 4H), 2.51 (s, 4H), 2.58 (br.s., 1H), 3.49 (d, J=2.93 Hz, 1H), 3.55-3.69 (m, 1H), 6.18-6.29 (m, 1H), 6.31 (br.s., 1H), 7.70 (d, J=8.20 Hz, 2H), 7.90 (d, J=7.62 Hz, 2H), 9.38 (br.s., 1H).

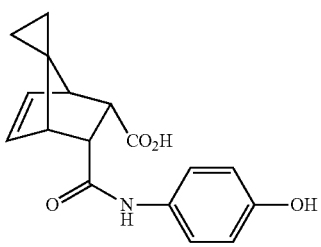

Compound 33

(+/−)-(1S,4R,5S,6R)-6-((4-Hydroxyphenyl)carbamoyl)spiro[bicyclo[2.2.1]hept[2]ene-7,1'-cyclopropane]-5-carboxylic Acid (Compound 33)

$^1$HNMR (300 MHz, CD$_3$OH): δ 0.40-0.60 (m, 4H), 2.48 (s, 2H), 3.46 (dd, J=3.0, 10.2 Hz, 1H), 3.55 (dd, J=3.0, 10.2 Hz, 1H), 6.24 (s, 1H), 6.36 (s, 1H), 6.68 (d, J=9.0 Hz, 2H), 7.24 (d, J=9.0 Hz, 2H).

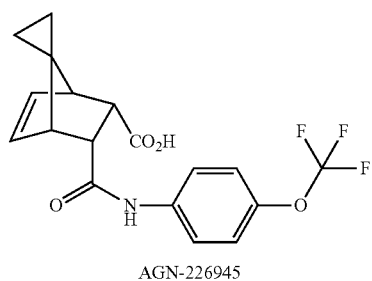

Compound 34

AGN-226945

(+/−)-(1S,4R,5S,6R)-6-β4-(Trifluoromethoxy)phenyl)carbamoyl)spiro[bicyclo-[2.2.1]hept[2]ene-7,1'-cyclopropane]-5-carboxylic Acid (Compound 34)

$^1$HNMR (300 MHz, acetone-d$_6$): δ 0.37-0.59 (m, 4H), 2.51 (br.s., 1H), 2.57 (br.s., 1H), 3.46 (dd, J=9.96, 3.52 Hz, 1H), 3.53-3.67 (dd, J=9.96, 3.52 Hz, 1H), 6.24 (m, 1H), 6.28-6.40 (m, 1H), 7.21 (d, J=8.79 Hz, 2H), 7.70 (d, J=9.08 Hz, 2H), 9.27 (br.s., 1H).

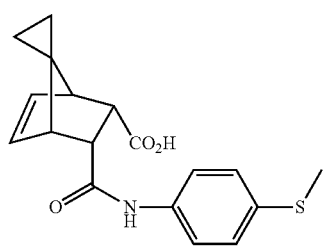

Compound 35

(+/−)-(1S,4R,5S,6R)-6-((4-(Methylthio)phenyl)carbamoyl)spiro[bicyclo-[2.2.1]hept[2]ene-7,1'-cyclopropane]-5-carboxylic Acid (Compound 35)

$^1$HNMR (300 MHz, acetone-d$_6$): δ 0.36-0.60 (m, 4H), 2.44 (s, 3H), 2.50 (br.s., 1H), 2.55 (br.s., 1H), 3.44 (dd, J=9.96, 3.22 Hz, 1H), 3.55-3.65 (dd, J=9.96, 3.22 Hz, 1H), 6.22 (dd, J=5.57, 2.93 Hz, 1H), 6.32 (dd, J=5.42, 2.78 Hz, 1H), 7.20 (d, J=8.50 Hz, 2H), 7.55 (d, J=8.79 Hz, 2H), 9.08 (br.s., 1H).

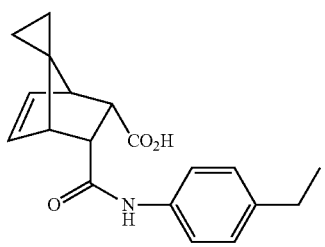

Compound 36

(+/−)-(1S,4R,5S,6R)-6-((4-Ethylphenyl)carbamoyl)spiro[bicyclo[2.2.1]hept[2]ene-7,1'-cyclopropane]-5-carboxylic Acid (Compound 36)

$^1$HNMR (300 MHz, acetone-d$_6$): δ 0.35-0.57 (m, 4H), 1.17 (t, J=7.47 Hz, 3H), 2.46-2.65 (m, 4H), 3.42 (dd, J=9.96, 3.52 Hz, 1H), 3.60 (dd, J=9.96, 3.52 Hz, 1H), 6.21 (dd, J=5.57, 2.93 Hz, 1H), 6.33 (dd, J=5.71, 2.78 Hz, 1H), 7.09 (d, J=8.20 Hz, 2H), 7.49 (d, J=8.50 hz, 2H), 8.99 (br.s., 1H).

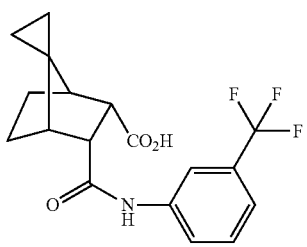

Compound 37

(+/−)-(1R,2S,3R,4S)-3-β3-(Trifluoromethyl)phenyl)carbamoyl)spiro[bicyclo-[2.2.1]heptane-7,1'-cyclopropane]-2-carboxylic Acid (Compound 37)

$^1$HNMR (300 MHz, CD$_3$OD): δ 0.46-0.73 (m, 4H), 1.71 (d, J=3.81 Hz, 4H), 1.77-1.94 (m, 2H), 2.11-2.26 (m, 1H), 3.16-3.27 (dd, J=11.43, 4.40 Hz, 1H), 3.45 (dd, J=11.43, 4.40 Hz, 1H), 7.26-7.37 (m, 1H), 7.45 (t, J=7.91 Hz, 1H), 7.69 (d, J=7.91 Hz, 1H), 7.98 (s, 1H).

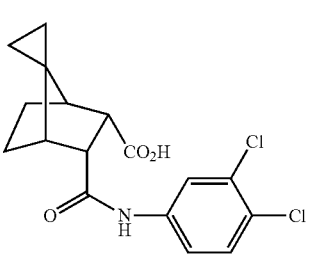

Compound 38

(+/−)-(1R,2S,3R,4S)-3-((3,4-Dichlorophenyl)carbamoyl)spiro[bicyclo[2.2.1]heptane-7,1'-cyclopropane]-2-carboxylic Acid (Compound 38)

$^1$HNMR (300 MHz, acetone-d$_6$): δ 0.36-0.70 (m, 4H), 1.44-1.75 (m, 4H), 1.81 (br.s., 1H), 2.20 (br.s., 1H), 3.16 (d, J=10.84 Hz, 1H), 3.41 (d, J=10.84 Hz, 1H), 7.43 (br.s., 2H), 8.06 (br.s., 1H), 9.34 (br.s., 1H)

Compound 39

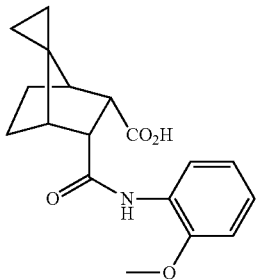

(+/−)-(1R,2S,3R,4S)-3-((2-Methoxyphenyl)carbamoyl)spiro[bicyclo[2.2.1]heptane-7,1'-cyclopropane]-2-carboxylic Acid (Compound 39)

$^1$HNMR (300 MHz, acetone-$d_6$): δ 0.47-0.70 (m, 4H), 1.55-1.74 (m, 4H), 1.81-1.83 (m, 2H), 2.23-2.38 (m, 1H), 2.81 (br.s., 1H), 3.16 m, 1H), 3.58-3.69 (m, 1H), 3.84 (s, 3H), 6.83-6.93 (m, 1H), 6.95-7.06 (m, 2H), 8.31 (d, J=8.20 Hz, 1H), 8.47 (br.s., 1H).

Compound 40

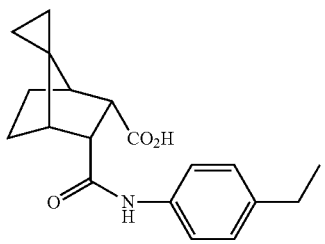

(+/−)-(1R,2S,3R,4S)-3-((4-Ethylphenyl)carbamoyl)spiro[bicyclo[2.2.1]heptane-7,1'-cyclopropane]-2-carboxylic Acid (Compound 40)

$^1$HNMR (300 MHz, CDCl$_3$): δ 0.50-0.70 (m, 4H), 1.20 (t, J=7.5 Hz, 3H), 1.62-1.90 (m, 5H), 2.02-2.20 (m, 1H), 2.57 (q, J=7.5 Hz, 2H), 3.20-3.38 (m, 2H), 7.12 (d, J=8.4 Hz, 2H), 7.37 (d, J=8.4 Hz, 2H).

Compound 41

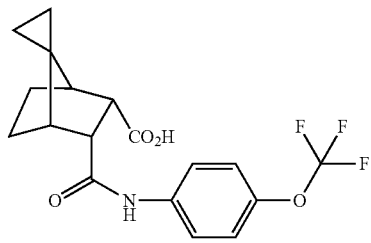

(+/−)-(1R,2S,3R,4S)-3-((4-(Trifluoromethoxy)phenyl)carbamoyl)spiro-[bicyclo[2.2.1]heptane-7,1'-cyclopropane]-2-carboxylic Acid (Compound 41)

$^1$HNMR (300 MHz, CD$_3$OD): δ 0.50-0.70 (m, 4H), 1.62-1.90 (m, 5H), 2.12-2.22 (m, 1H), 3.21 (d, J=10.8 Hz, 1H), 3.43 (d, J=10.8 Hz, 1H), 7.17 (d, J=8.4 Hz, 2H), 7.59 (d, J=8.4 Hz, 2H).

Compound 42

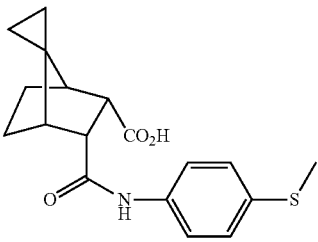

(+/−)-(1R,2S,3R,4S)-3-((4-(Methylthio)phenyl)carbamoyl)spiro[bicyclo-[2.2.1]heptane-7,1'-cyclopropane]-2-carboxylic Acid (Compound 42)

$^1$HNMR (300 MHz, CD$_3$OD): δ 0.50-0.65 (m, 4H), 1.60-1.85 (m, 5H), 2.18-2.24 (m, 1H), 2.43 (s, 3H), 3.18 (d, J=11.4 Hz, 1H), 3.43 (d, J=11.4 Hz, 1H), 7.22 (d, J=9.0 Hz, 2H), 7.43 (d, J=9.0 Hz, 2H).

Compound 43

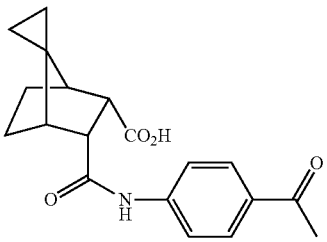

(+/−)-(1S,2R,3S,4R)-2-((4-Acetylphenyl)carbamoyl)spiro[bicyclo[2.2.1]heptane-7,1'-cyclopropane]-3-carboxylic Acid (Compound 43)

$^1$HNMR (300 MHz, CD$_3$OD): δ 0.50-0.70 (m, 4H), 1.60-1.88 (m, 5H), 2.18 (brs, 1H), 2.54 (s, 3H), 3.21 (d, J=10.8 Hz, 1H), 3.45 (d, J=10.8 Hz, 1H), 7.65 (d, J=7.8 Hz, 2H), 7.92 (d, J=7.8 Hz, 2H).

Compound 44

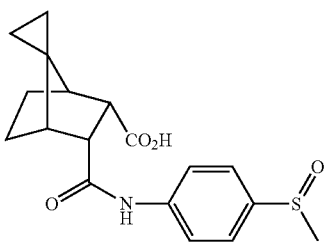

(+/−)-(1R,2S,3R,4S)-3-((4-(Methylsulfinyl)phenyl)carbamoyl)spiro[bicyclo-[2.2.1]heptane-7,1'-cyclopropane]-2-carboxylic Acid (Compound 44)

$^{1}$HNMR (300 MHz, CD$_3$OD): δ 0.51-0.73 (m, 4H), 1.72 (br.s., 4H), 1.76-1.91 (m, 2H), 2.12-2.26 (m, 1H), 2.77 (s, 3H), 3.22 (d, J=10.84 Hz, 1H), 3.45 (d, J=10.84 Hz, 1H), 7.63 (d, 2H), 7.77 (d, J=8.79 Hz, 2H), 7.89 (s, 1H).

Compound 45

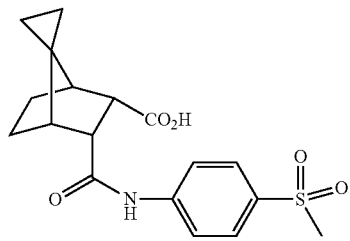

(1R,2S,3R,4S)-3-((4-(Methylsulfonyl)phenyl)carbamoyl)spiro[bicyclo[2.2.1]heptane-7,1'-cyclopropane]-2-carboxylic Acid (Compound 45).

$^{1}$HNMR (300 MHz, CD$_3$OD): δ 0.61 (m, 4H), 1.70 (br.s., 4H), 1.81 (br.s., 1H), 1.86-1.93 (m, 1H), 3.08 (s, 3H), 3.37-3.50 (m, 2H), 7.70-7.93 (m, 4H).

Compound 46

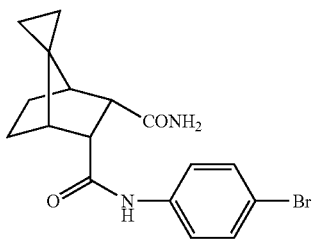

(+/−)-(1S,2R,3S,4R)—N$^2$-(4-bromophenyl)spiro[bicyclo[2.2.1]heptane-7,1'-cyclopropane]-2,3-dicarboxamide (Compound 46). General Procedure C To a solution of starting material (0.30 g, 0.83 mmol) in THF (15.0 mL) at ambient temperature was added 1,1'-carbonyl bis-1H-imidazole (0.15 g, 0.91 mmol), and the reaction was stirred for 2 h. NH$_4$OH 28-30% (1.50 mL) was added, and the reaction was stirred for 10 min, then acidified with 2N HCl to pH=1. The mixture was extracted with EtOAc, dried over MgSO$_4$, and filtered. The solvent was removed, and the residue was purified by preparative TLC (MeOH/CH$_2$Cl$_2$=5/95) to afford 0.0658 g (22%) of the desired product as a white solid.

$^{1}$HNMR (300 MHz, CD$_3$OD): δ 0.61 (br.s., 4H), 1.61-1.83 (m, 4H), 1.96-2.12 (m, 2H), 3.31 (br.s., 2H), 7.32-7.41 (m, 2H), 7.42-7.51 (m, 2H).

Racemic Compound 46 was Separated into Individual Enantiomers 46A and 46B

Absolute Stereochemistry Determined by X-ray Crystallography

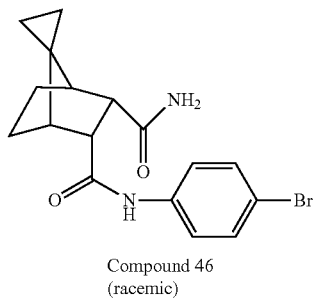

Compound 46 (racemic)

Chiral chromatography

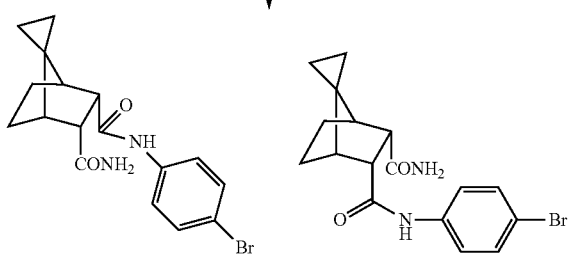

[α] = + 33.4°
c = 1.00, MeOH
Compound 46A

[α] = − 34.0°
c = 1.01, MeOH
Compound 46B

Additional Compounds that were Prepared by General Procedure C

Compound 47

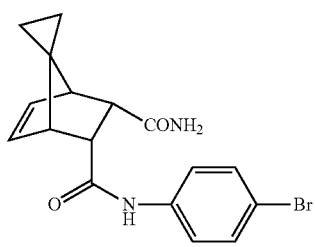

(+/−)-(1R,4S,5R,6S)—N-5-(4-Bromophenyl)spiro[bicyclo[2.2.1]hept[2]ene-7,1'-cyclopropane]-5,6-dicarboxamide (Compound 47)

$^{1}$HNMR (300 MHz, CD$_3$OD): δ 0.39-0.63 (m, 4H), 2.50 (s, 2H), 3.52 (s, 2H), 6.27-6.34 (m, 1H), 6.38-6.47 (m, 1H), 7.29-7.52 (m, 4H).

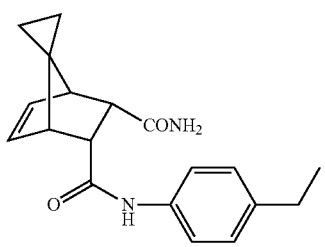

Compound 48

(+/−)-(1R,4S,5R,6S)—N-5-(4-Ethylphenyl)spiro[bicyclo[2.2.1]hept[2]ene-7,1'-cyclopropane]-5,6-dicarboxamide (Compound 48)

¹HNMR (300 MHz, CDCl₃): δ 0.46 (d, J=5.86 Hz, 2H), 0.58 (d, J=7.33 Hz, 2H), 1.05-1.34 (m, 3H), 2.41-2.71 (m 4H), 3.54 (d, J=8.50 Hz, 2H), 6.54 (br.s., 1H), 6.59 (br.s., 1H), 7.11 (d, J=8.20 Hz, 2H), 7.33 (d, J=7.62 Hz, 2H), 7.86 (br.s., 1H).

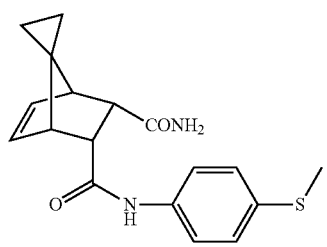

Compound 49

(+/−)-(1R,4S,5R,6S)—N-5-(4-(Methylthio)phenyl)spiro[bicyclo[2.2.1]hept[2]ene-7,1'-cyclopropane]-5,6-dicarboxamide (Compound 49)

¹HNMR (300 MHz, CD₃OD): δ 0.41-0.63 (m, 4H), 2.42 (s, 3H), 2.51 (br.s., 2H), 3.52 (br.s., 2H), 6.32 (br.s., 1H), 6.36-6.48 (m, 1H), 7.19 (d, J=8.50 Hz, 2H), 7.42 (d, J=8.50 Hz, 2H).

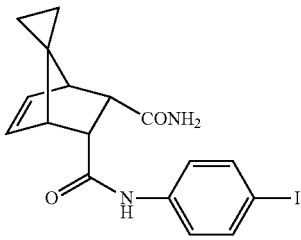

Compound 50

(+/−)-(1R,4S,5R,6S)—N-5-(4-Iodophenyl)spiro[bicyclo[2.2.1]hept[2]ene-7,1'-cyclopropane]-5,6-dicarboxamide (Compound 50)

¹HNMR (300 MHz, CD₃OD): δ 0.42-0.60 (m, 4H), 2.50 (br.s., 2H), 3.51 (s, 2H), 6.31 (m, 1H), 6.40 (m, 1H), 7.30 (d, J=8.50 Hz, 2H), 7.56 (d, J=8.50 Hz, 2H).

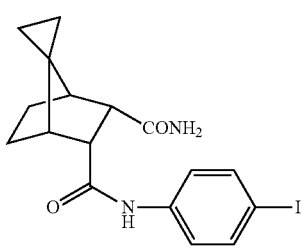

Compound 51

(+/−)-(1S,2R,3S,4R)—N2-(4-Iodophenyl)spiro[bicyclo[2.2.1]heptane-7,1'-cyclopropane]-2,3-dicarboxamide (Compound 51)

¹HNMR (300 MHz, CD₃OD): δ 0.61 (br.s., 4H), 1.76 (m, 4H), 1.96-2.12 (m, 2H), 3.31 (br.s., 2H), 7.33 (d, 8.79 Hz, 2H), 7.57 (d, J=8.79 Hz, 2H).

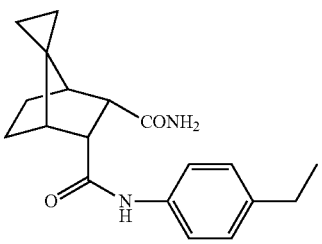

Compound 52

(+/−)-(1S,2R,3S,4R)—N²-(4-Ethylphenyl)spiro[bicyclo[2.2.1]heptane-7,1'-cyclopropane]-2,3-dicarboxamide (Compound 52)

¹HNMR (300 MHz, CD₃OD): δ 0.52-0.69 (m 4H), 1.19 (m, 3H), 1.61-1.84 (m, 4H), 2.04 (d, J=8.20 Hz, 2H), 2.58 (d, J=7.62 Hz, 2H), 3.30 (br.s., 2H), 7.10 (d, J=8.20 Hz, 2H), 7.39 (d, J=8.50 Hz, 2H).

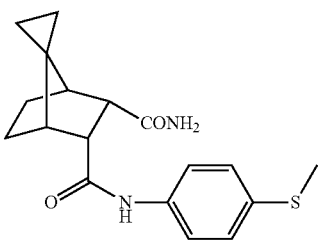

Compound 53

(+/−)-(1S,2R,3S,4R)—N2-(4-(Methylthio)phenyl)spiro[bicyclo[2.2.1]heptane-7,1'-cyclopropane]-2,3-dicarboxamide (Compound 53)

¹HNMR (300 MHz, CD₃OD): δ 0.53-0.70 (m, 4H), 1.64-1.84 (m, 4H), 1.96-2.08 (m, 2H), 2.43 (s, 3H), 3.16-3.28 (m, 2H), 7.20 (d, J=8.79 Hz, 2H), 7.45 (d, J=8.50 Hz, 2H).

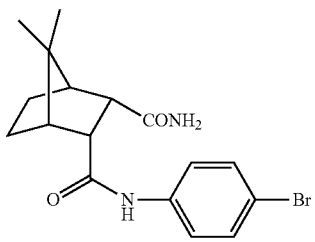

Compound 54

(+/−)-(1S,2R,3S,4R)—N2-(4-Bromophenyl)-7,7-dimethylbicyclo[2.2.1]heptane-2,3-dicarboxamide (Compound 54)

¹HNMR (CDCl₃): δ 1.12 (d, J=14.36 Hz, 6H), 1.69-2.08 (m, 6H), 3.23 (br.s., 1H), 3.27-3.41 (m, 1H), 5.70 (br.s., 2H), 7.32-7.42 (m, 2H), 7.42-7.53 (m, 2H), 9.12 (br.s., 1H).

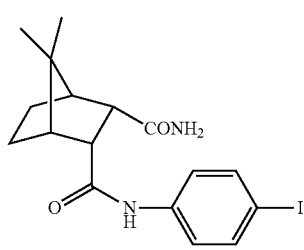

Compound 55

(+/−)-(1S,2R,3S,4R)—N2-(4-Iodophenyl)-7,7-dimethylbicyclo[2.2.1]heptane-2,3-dicarboxamide (Compound 55)

¹HNMR (300 MHz, CDCl₃): δ 1.09 (d, J=7.62 hz, 6H), 1.51-2.05 (m, 6H), 3.13-3.27 (m, 1H), 3.32 (br.s., 1H), 5.84 (br.s., 2H), 7.33 (d, J=8.20 Hz, 2H), 7.54 (d, J=8.20 Hz, 2H), 9.11 (br.s., 1H).

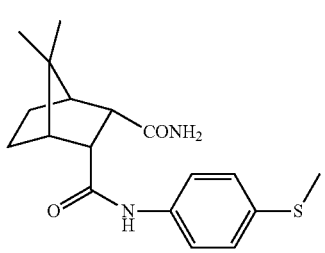

Compound 56

(+/−)-(1S,2R,3S,4R)-7,7-Dimethyl-N2-(4-(methylthio)phenyl)bicyclo[2.2.1]heptane-2,3-dicarboxamide (Compound 56)

¹HNMR (300 MHz, CDCl₃): δ 1.09 (d, J=10.84 Hz, 6H), 1.61-2.06 (m, 6H), 2.44 (s, 3H), 3.21 (m, 1H), 3.34 (m, 1H), 5.93 (br.s., 1H), 7.19 (d, J=8.20 Hz, 2H), 7.49 (d, J=8.20 Hz, 2H), 8.80-9.01 (m, 1H).

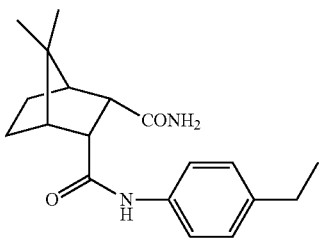

Compound 57

(+/−)-(1S,2R,3S,4R)—N2-(4-Ethylphenyl)-7,7-dimethylbicyclo[2.2.1]heptane-2,3-dicarboxamide (Compound 57)

¹HNMR (300 MHz, CDCl₃): δ 1.03-1.32 (m, 9H), 1.75 (br.s., 2H), 2.00 (br.s., 4H), 2.60 (q, J=7.52 Hz, 2H), 3.24 (m., 1H), 3.28-3.42 (m, 1H), 7.12 (d, J=8.20 Hz, 2H), 7.44 (d, J=7.91 Hz, 2H).

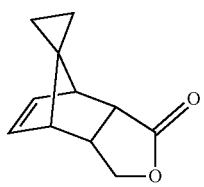

Intermediate A (+/−)-(3aR,4S,7R,7aS)-3a,4,7,7a-Tetrahydrospiro[4,7-methanoisobenzofuran-8,1'-cyclopropan]-1(3H)-one (Intermediate A)

To a solution of Compound 1 (760 mg, 4 mmol) in THF (10 mL) was added LiBH₄ (99 mg, 4.5 mmol) at ambient temp. The mixture was stirred for 16 h, then quenched with 5% H₂SO₄ in water (15 mL), and the product was extracted with CH₂Cl₂ (3×20 mL). The combined organic layers were washed with brine, and dried (MgSO₄), and concentrated under vacuum. The residue was purified by flash chromatography on silica gel using 30% EtOAc in hexane as the eluent. The title compound, Intermediate A, was isolated as a white solid.

¹HNMR (300 MHz, CDCl₃): δ 0.40-0.60 (m, 4H), 2.45 (brs, 1H), 2.70 (brs, 1H), 3.20-3.31 (m, 1H), 3.40 (dd, J=4.5, 9.6 Hz, 1H), 3.85 (dd, J=3.6, 9.6 Hz, 1H), 4.31 (t, J=9.0 Hz, 1H), 6.38 (brs, 2H).

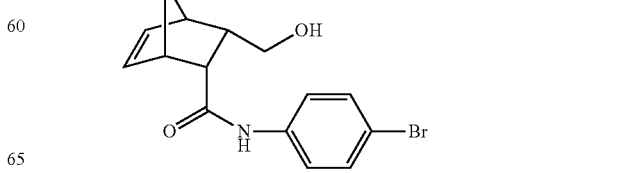

Compound 58

(+/−)-(1R,4S,5R,6S)—N-(4-Bromophenyl)-6-(hydroxymethyl)spiro[bicyclo[2.2.1]-hept[2]ene-7,1'-cyclopropane]-5-carboxamide (Compound 58)

To a solution of 4-bromoaniline (390 mg, 2.3 mmol) in THF (5 mL) at ambient temperature was added n-BuLi (2.5M solution in hexane, 0.72 mL, 1.8 mmol). After 30 min at ambient temperature, a solution of Intermediate A (190 mg, 1.1 mmol) in THF (5 mL) was added. The reaction mixture was stirred for 3 h, and then quenched by the addition of EtOAc (25 mL) and water (5 mL). This mixture was washed with brine, the layers separated and the organic layer was dried (MgSO$_4$), and concentrated under reduced pressure. The residue was titutrated with CCl$_4$ (5 mL) to give the title compound as a solid.

$^1$HNMR (300 MHz, CD$_3$OD): δ 0.40-0.60 (m, 4H), 2.35 (s, 1H), 2.43 (s, 1H), 2.80-2.92 (m, 1H), 3.30-3.58 (m, 3H), 6.21 (d, J=5.7 Hz, 1H), 6.37 (d, J=5.7 Hz, 1H), 7.40 (d, J=7.8 Hz, 2H), 7.44 (d, J=7.8 Hz, 2H).

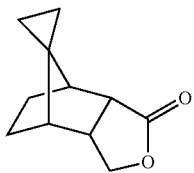

Intermediate B

(+/−)-(3aR,4S,7R,7aS)-Hexahydrospiro[4,7-methanoisobenzofuran-8,1'-cyclopropan]-1(3H)-one (Intermediate B)

To a solution of Compound 2 (450 mg, 2.3 mmol) in THF (10 mL) was added LiBH$_4$ in THF (2M soln. 1.4 mL, 2.8 mmol) at ambient temperature. The mixture was stirred for 1 h, and the reaction was quenched with 5% H$_2$SO$_4$ in water (10 mL). The solution was diluted with 25 mL of EtOAc, the layers separated, and the product was extracted from the aqueous layer with EtOAc (2×25 mL). The combined organic layers were washed with brine, and dried (MgSO4), and the solvents were concentrated under vacuum. The residue was purified by flash chromatography on silica gel using 25% EtOAc in hexane as the eluent. The title compound, Intermediate B, was isolated as a white solid after removal of the solvent under vacuum.

$^1$HNMR (300 MHz, CDCl$_3$): δ 0.52-0.64 (m, 4H), 1.50-1.65 (m, 2H), 1.65-1.95 (m, 4H), 3.10-3.22 (m, 2H), 4.22-4.38 (m, 2H).

Compound 59

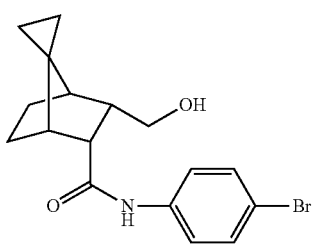

(+/−)-(1S,2R,3S,4R)—N-(4-Bromophenyl)-3-(hydroxymethyl)spiro[bicyclo[2.2.1]-heptane-7,1'-cyclopropane]-2-carboxamide (Compound 59)

Compound 59 was prepared from Intermediate B by using the same procedure used to prepare Compound 58.

$^1$HNMR (300 MHz, CD$_3$OD): δ 0.50-0.70 (m, 4H), 1.55-1.75 (m, 4H), 1.80 (t, J=8.1 Hz, 1H), 2.04 (t, J=8.1 Hz, 1H), 2.42-2.60 (m, 1H), 3.16 (dd, J=3.9, 11.4 Hz, 1H), 3.80-3.95 (m, 2H), 7.40 (d, J=7.8 Hz, 2H), 7.46 (d, J=7.8 Hz, 2H).

Compound 60

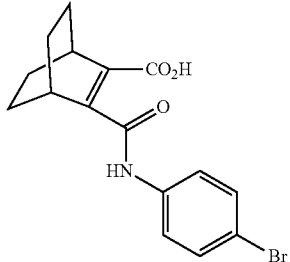

(1s,4s)-3-((4-Bromophenyl)carbamoyl)bicyclo[2.2.2]oct-2-ene-2-carboxylic Acid (Compound 60)

Bicyclo[2.2.2]oct-2-ene-2,3-dicarboxylic anhydride (Alfa Aesar Co., 212 mg, 1.2 mmol), 4-bromoaniline (172 mg, 1.0 mmol) and 4.8 mL of chloroform were stirred overnight at room temperature. The solid that formed was separated by filtration and washed 3 times with cold chloroform. The solid was dried to yield the title compound as a white solid.

$^1$HNMR (300 MHz, acetone-d$_6$): δ 1.31-1.49 (m, 4H), 1.60-1.72 (m, 4H), 3.06 (s, 1H), 3.23 (s, 1H), 7.48 (d, 2H, J=8.8 Hz), 7.66 (d, 2H, J=8.8 Hz), 9.67 (s, 1H), 11.45 (s, 1H).

Additional Compounds that were Prepared by General Procedure C

Compound 61

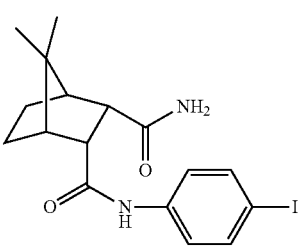

(+/−)-(1S,2R,3S,4R)—N$^2$-(4-Iodophenyl)-7,7-dimethylbicyclo[2.2.1]heptanes-2,3-dicarboxamide (Compound 61)

$^1$HNMR (300 MHz, CDCl$_3$): δ 1.09 (s, 6H), 1.51-2.05 (m, 6H), 3.13-3.27 (m, 1H), 3.32 (br. s., 1H), 7.33 (d, J=8.2 Hz, 2H), 7.54 (d, J=8.2 Hz, 2H).

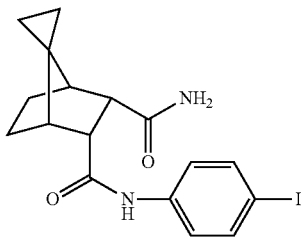

Compound 62

(+/−)-(1S,2R,3S,4R)—N²-(4-Iodophenyl)-[bicyclo[2.2.1]heptane-7,1'-cyclopropane]-2,3-dicarboxamide (Compound 62)

¹HNMR (300 MHz, CD₃OD): δ 0.61 (br.s, 4H), 1.74-1.85 (m, 4H), 1.98-2.05 (m, 2H), 3.25-3.34 (m, 2H), 7.33 (d, J=8.2 Hz, 2H), 7.57 (d, J=8.2 Hz, 2H).

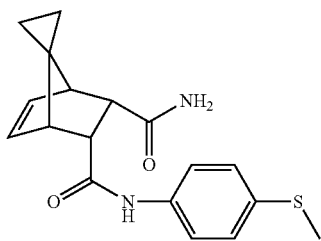

Compound 63

(+/−)-(1R,4S,5R,6S)—N⁵-(4-(Methylthio)phenyl)spiro[bicyclo[2.2.1]hept[2]ene-7,1'-cyclopropane]-5,6-dicarboxamide (Compound 63)

¹HNMR (300 MHz, CD₃OD): δ 0.45-60 (m, 4H), 2.42 (s, 3H), 2.51 (s, 2H), 3.50-3.58 (m, 2H), 6.32 (s, 1H), 6.45 (s, 1H), 7.19 (d, J=6.0 Hz, 2H), 7.42 (d, J=6.0 Hz, 2H).

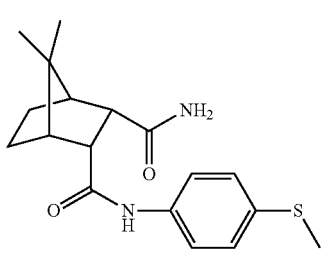

Compound 64

(+/−)-(1S,2R,3S,4R)-7,7-Dimethyl-N²-(4-(methylthio)phenyl)bicyclo[2.2.1]heptane-2,3-dicarboxamide (Compound 64)

¹HNMR (300 MHz, CDCl₃): δ 1.07 (s, 3H), 1.11 (s, 3H), 1.67-2.05 (m, 6H), 2.44 (s, 3H), 3.10-3.40 (m, 2H), 7.19 (d, J=8.2 Hz, 2H), 7.49 (d, J=8.2 Hz, 2H).

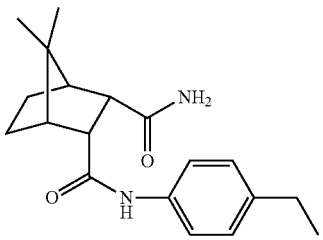

Compound 65

(+/−)-(1S,2R,3S,4R)—N²-(4-Ethylphenyl)-7,7-dimethyl-bicyclo[2.2.1]heptane-2,3-dicarboxamide (Compound 65)

¹HNMR (300 MHz, CDCl₃): δ 1.09 (s, 3H), 1.15 (s, 3H), 1.20 (t, J=7.5 Hz, 3H), 1.50-1.80 (m, 2H), 1.80-2.02 (m, 4H), 2.60 (q, J=7.52 Hz, 2H), 3.22-3.40 (m, 2H), 7.12 (d, J=8.20 Hz, 2H), 7.44 (d, J=8.20 Hz, 2H).

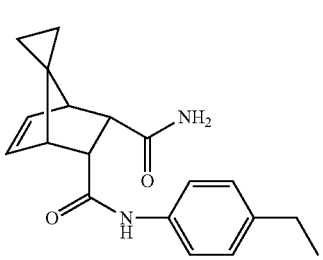

Compound 66

(+/−)-(1R,4S,5R,6S)—N⁵-(4-Ethylphenyl)spiro[bicyclo[2.2.1]hept[2]ene-7,1'-cyclopropane]-5,6-dicarboxamide (Compound 66)

¹HNMR (300 MHz, CDCl₃): δ 0.46 (d, J=5.86 Hz, 2H), 0.58 (d, J=5.86 Hz, 2H), 1.19 (t, J=8.50 Hz, 3H), 2.41-2.71 (m, 4H), 3.54 (q, J=8.50 Hz, 2H), 6.54 (s, 1H), 6.59 (s, 1H), 7.11 (d, J=8.20 Hz, 2H), 7.33 (d, J=8.20 Hz, 2H).

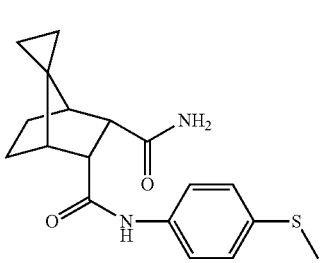

Compound 67

(+/−)-(1S,2R,3S,4R)—N²-(4-(Methylthio)phenyl)-spiro[bicyclo[2.2.1]heptane-7,1'-cyclopropane]-2,3-dicarboxamide (Compound 67)

¹HNMR (300 MHz, CD₃OD): δ 0.53-0.70 (m, 4H), 1.64-1.84 (m, 4H), 1.96-2.08 (m, 2H), 2.43 (s, 3H), 3.16-3.28 (m, 2H), 7.20 (d, J=8.50 Hz, 2H), 7.45 (d, J=8.50 Hz, 2H).

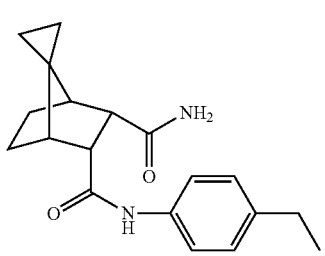

Compound 68

(+/−)-(1S,2R,3S,4R)—N²-(4-Ethyl-phenyl)-spiro[bicyclo[2.2.1]heptane-7,1'-cyclopropane]-2,3-dicarboxamide (Compound 68)

¹HNMR (300 MHz, CD₃OD): δ 0.52-0.69 (m, 4H), 1.19 (t, J=7.62 Hz, 3H), 1.61-1.84 (m, 4H), 2.04 (d, J=8.20 Hz, 2H), 2.58 (q, J=7.62 Hz, 2H), 3.20-3.35 (m, 2H), 7.10 (d, J=8.20 Hz, 2H), 7.39 (d, J=8.20 Hz, 2H).

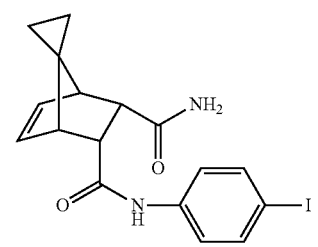

Compound 69

(+/−)-(1R,4S,5R,6S)—N⁵-(4-Iodophenyl)spiro[bicyclo[2.2.1]hept[2]ene-7,1'-cyclopropane]-5,6-dicarboxamide (Compound 69)

¹HNMR (300 MHz, CDCl₃): δ 0.42-0.60 (m, 4H), 2.50 (br. s., 2H), 3.51 (s, 2H), 6.31 (dd, J=3.81, 1.76 Hz, 1H), 6.40 (dd, J=3.81, 1.76 Hz, 1H), 7.30 (d, J=8.50 Hz, 2H), 7.56 (d, J=8.50 Hz, 2H).

Additional Compounds that were Prepared by General Procedure A

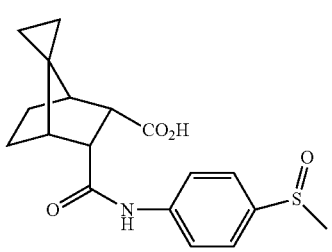

Compound 70

(+/−)-(1R,2S,3R,4S)-3-((4-Methylsulfinyl)phenyl)carbamoyl)spiro[bicyclo[2.2.1]-heptane-7,1'-cyclopropane]-2-carboxylic Acid (Compound 70)

¹HNMR (300 MHz, CD₃SOCD₃): δ 0.51-0.73 (m, 4H), 1.72 (br.s., 4H), 1.76-1.91 (m, 2H), 2.12-2.26 (m, 1H), 2.77 (s, 3H), 3.22 (d, J=10.84 Hz, 1H), 3.45 (dd, J=10.84, 4.40 Hz, 1H), 7.63 (d, J=8.79 Hz, 2H), 7.77 (d, J=8.79 Hz, 2H).

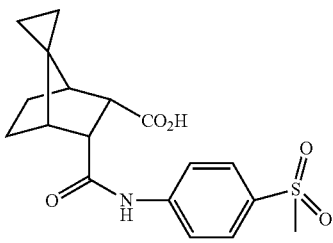

Compound 71

(+/−)-(1R,2S,3R,4S)-3-((4-(Methylsulfonyl)phenyl)carbamoyl)spiro[bicyclo[2.2.1]-heptane-7,1'-cyclopropane]-2-carboxylic Acid (Compound 71)

¹HNMR (300 MHz, CD₃SOCD₃): δ 0.61 (t, J=8.94 Hz, 4H), 1.70 (br.s., 4H), 1.76-1.91 (m, 2H), 3.40 (s, 3H), 3.30 (br.s., 1H), 3.45 (br.s., 1H), 7.70-7.93 (m, 4H).

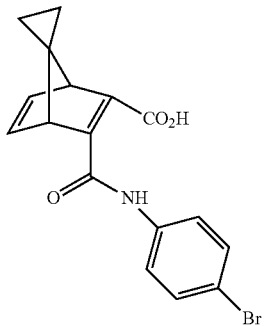

Compound 72

(+/−)-(1R,4S)-2-((4-Bromophenyl)carbamoyl)spiro[bicyclo[2.2.1]-hepta[2,5]diene-7,1'-cyclopropane]-3-carboxylic Acid (Compound 72)

¹HNMR (300 MHz, CD₃COCD₃): δ 0.44-0.061 (m, 4H), 3.34 (d, J=8.5 Hz, 2H), 6.50-6.70 (m, 2H), (7.01 (d, J=8.2 Hz, 2H), 7.36 (d, J=8.2 Hz, 2H).

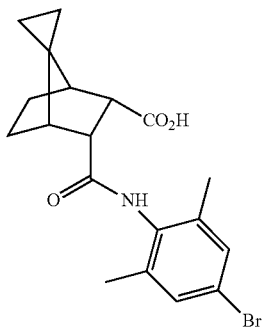

Compound 73

(+/−)-(1R,2S,3R,4S)-2-((4-Bromo-2,6-dimethylphenyl)carbamoyl)spiro[bicyclo[2.2.1]-heptane-7,1'-cyclopropane]-3-carboxylic Acid (Compound 73)

¹HNMR (300 MHz, CD₃COCD₃): δ 0.70-0.85 (m. 4H), 1.66 (br.s., 4H), 1.65-1.55 (s, 6H), 3.18 (d, J=3H), 3.30 (br.s., 1H), 3.60 (br.s., 1H), 7.25 (br. s., 4H).

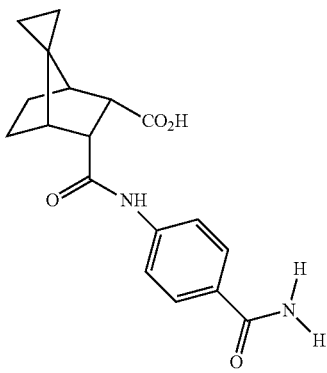

Compound 74

(+/−)-(1S,2R,3S,4R)-2-((4-Carbomoylphenyl)carbamoyl)spiro[bicyclo[2.2.1]-heptan-7,1'-cyclopropane]-3-carboxylic Acid (Compound 74)

¹HNMR (300 MHz, CD₃OD): δ 0.55-0.70 (m, 4H), 1.63 (br.s., 3H), 1.75-1.92 (m, 2H), 2.05-2.25 (m, 2H), 3.20 (dd, J=4.5.0, 2.0 Hz, 1H), 3.45 (dd, J=4.5, 2.0 Hz, 1H), 7.60 (d, J=8.00 Hz, 2H), 7.80 (m, 4H).

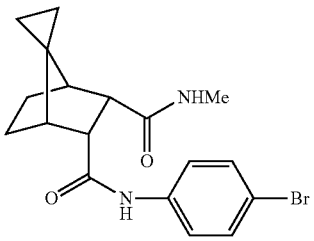

Compound 75

(+/−)-(1S,2R,3S,4R)-2-((4-Acetamidophenyl)carbamoyl)spiro[bicyclo[2.2.1]-heptan-7,1'-cyclopropane]-3-carboxylic Acid (Compound 75)

¹HNMR (300 MHz, CD₃OD): δ 0.55-0.72 (m, 4H), 1.70 (br.s., 3H), 1.80-1.92 (m, 2H), 2.05 (s, 3H), 2.20-2.25 (m, 1H), 3.20 (dd, J=4.5, 2.0 Hz, 1H), 3.45 (dd, J=4.5, 2.0 Hz, 1H), 7.45 (s, 4H).

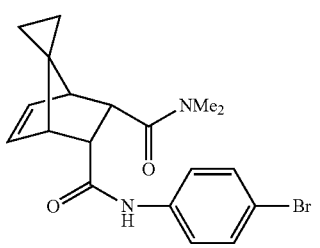

Compound 76

(+/−)-(1S,4S,5R,6S)—N⁵-(4-Bromophenyl)-N⁶,N⁶-dimethylspiro[bicyclo[2.2.1]hept[2]ene]-7,1'-cyclopropane]-5,6-dicarboxamide (Compound 76): General Procedure D.

To compound (CAS #359434-59-6) (260 mg, 0.74 mmol), CH₂Cl₂ (5 mL) was added Et₃N (231 mg, 2.29 mmol). This solution was cooled to −30° C. and a solution of ClCO₂Et (124 mg, 1.15 mmol) in CH₂Cl₂ (3 mL) was added via canula. The mixture was stirred for 15 min, then dimethylamine in THF (2M solution, 1 mL) was added to the reaction. After warming to ambient temperature the solid formed was collected by filtration. This solid was partially dissolved in EtOAC (5 mL), MeOH (2 mL), and water (2 mL) and mixed well in a separatory funnel. The product (Compound 62) was the insoluble solid and was collected by filtration as a white solid.

¹HNMR (300 MHz, CD₃SOCD₃): δ 0.44 (s, 4H), 2.35 (s, 1H), 2.53 (s, 1H), 2.64 (s, 3H), 2.82 (s, 3H), 3.42 (d, J=7.2 Hz, 1H), 3.55 (d, J=7.2 Hz, 1H), 5.87 (s, 1H), 6.35 (s, 1H), 7.41 (s, 4H).

Additional Compounds that were Prepared by General Procedure D

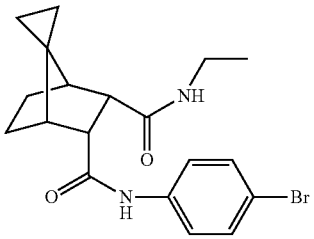

Compound 77

(+/−)-(1S,2R,3S,4R)—N²-(4-Bromophenyl)-N³-methylspiro[bicyclo[2.2.1]heptane-7,1'-cyclopropane]-2,3-dicarboxamide (Compound 77)

¹HNMR (300 MHz, CD₃OD): δ 0.55-0.70 (m, 4H), 1.62-1.80 (m, 4H), 1.95-2.05 (m, 2H), 2.68 (s, 3H), 3.15-3.38 (m, 2H), 7.38 (d, J=8.2 Hz, 2H), 7.47 (d, J=8.2 Hz, 2H).

Compound 78

(+/−)-(1S,2R,3S,4R)—N²-(4-Bromophenyl)-N³-ethylspiro[bicyclo[2.2.1]heptane-7,1'-cyclopropane]-2,3-dicarboxamide (Compound 78)

¹HNMR (300 MHz, CD₃OD): δ 0.55-0.70 (m, 4H), 1.06 (t, J=7.2 Hz, 3H), 1.65-1.80 (m, 4H), 1.95-2.05 (m, 2H), 3.15 (q, J=8.2 Hz, 2H), 3.20-3.35 (m, 2H), 7.38 (d, J=8.2 Hz, 2H), 7.46 (d, J=8.2 Hz, 2H).

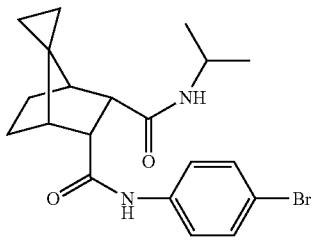

Compound 79

(+/−)-(1S,2R,3S,4R)—N²-(4-Bromophenyl)-N³-isopropylspiro[bicyclo[2.2.1]heptane-7,1'-cyclopropane]-2,3-dicarboxamide (Compound 79)

¹HNMR (600 MHz, CD₃OD): δ 0.55-0.70 (m, 4H), 1.05 (d, J=6.6 Hz, 3H), 1.09 (d, J=6.6 Hz, 3H), 1.65-1.80 (m, 4H), 1.95-2.00 (m, 1H), 2.10-2.15 (m, 1H), 3.21 (dd, J=3.6, 7.2 Hz, 1H), 3.26 (dd, J=3.60, 7.2 Hz, 1H), 3.91 (sept, 1H), 7.38 (d, J=8.2 Hz, 2H), 7.46 (d, J=8.2 Hz, 2H).

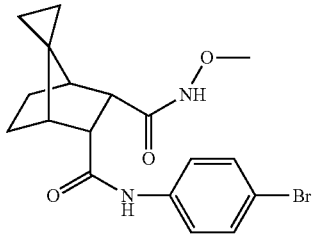

Compound 80

(+/−)-(1S,2R,3S,4R)—N²-(4-Bromophenyl)-N³-methoxyspiro[bicyclo[2.2.1]heptane-7,1'-cyclopropane]-2,3-dicarboxamide (Compound 80)

¹HNMR (600 MHz, CD₃SOD₃): δ 0.50-0.75 (m, 4H), 1.50-1.75 (m, 4H), 1.98 (br.s., 2H), 3.01 (br.s., 1H), 3.20 (br.s., 1H), 3.50 (s, 3H), 7.41 (d, J=8.2 Hz, 2H), 7.52 (d, J=8.2 Hz, 2H).

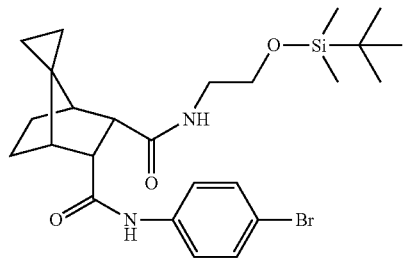

Compound 81

(+/−)-(1S,2R,3S,4R)—N²-(4-Bromophenyl)-N³-[2-((tert-butyldimethylsilyl)oxy)ethyl]spiro[bicyclo[2.2.1]heptane-7,1'-cyclopropane]-2,3-dicarboxamide (Compound 81)

¹HNMR (600 MHz, CDCl₃): δ 0.01 (s, 6H), 0.45-0.70 (m, 4H), 0.83 (s, 9H), 1.55-1.80 (m, 5H), 2.05-2.15 (m, 1H), 3.01-3.08 (m, 1H), 3.32-3.45 (m, 3H), 3.60-3.70 (m, 2H), 7.19 (d, J=8.8 Hz, 2H), 7.32 (d, J=78.8 Hz, 2H).

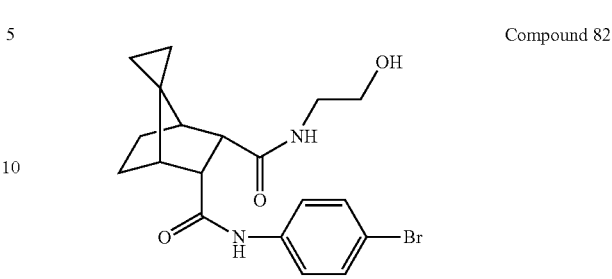

Compound 82

(+/−)-(1S,2R,3S,4R)—N²-(4-Bromophenyl)-N³-[2-hydroxyethyl]spiro[bicyclo[2.2.1]heptane-7,1'-cyclopropane]-2,3-dicarboxamide (Compound 82)

To a cold (0° C.) solution of compound 81 (46 mg, 0.084 mmol) in THF (5 mL) was added HF-pyridine (0.5 mL). The reaction mixture was warmed to ambient temperature and stirred for 2 h. After which time aq. NaHCO₃ (1 M, 10 mL) was added and extracted with CH₂Cl₂ (2×20 mL). The organic layer was washed with brine and dried with MgSO₄. The solid was filtered and from the filtrate solvent was removed under reduced pressure. The crude product was purified by silicagel prep. TLC. The product (compound 82) was isolated as a white solid.

¹HNMR (600 MHz, CD₃OD): δ 0.45-0.70 (m, 4H), 1.65-1.80 (m, 4H), 1.95-2.15 (m, 2H), 3.20-3.40 (m, 4H), 3.56 (t, J=6.0 Hz, 2H), 7.38 (d, J=9.0 Hz, 2H), 7.46 (d, J=9.0 Hz, 2H).

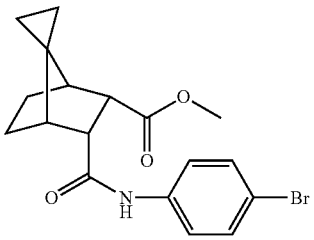

Compound 83

(+/−)-(1S,4S,5R,6S)-Methyl 2-((4-bromophenyl)carbamoyl)spiro[bicyclo[2.2.1]heptane-7,1'-cyclopropane]-3-carboxylate (Compound 83): General Procedure E To compound 10 (200 mg, 0.55 mmol), CH₂Cl₂ (5 mL) was added Et₃N (231 mg, 2.29 mmol). This solution was cooled to −30° C. and a solution of ClCO₂Et (124 mg, 1.15 mmol) in CH₂Cl₂ (3 mL) was added via canula. The mixture was stirred for 15 min, then MeOH (0.5 mL) was added to the reaction. After warming to ambient temperature the solvent was removed and the crude product was purified by silicagel chromatography. The pure product (Compound 83) was isolated as a white solid.

¹HNMR (300 MHz, CDCl₃): δ 0.44-0.65 (m, 4H), 1.60-1.80 (m, 5H), 2.10-2.28 (m, 1H), 3.15 (d, J=7.2 Hz, 1H), 3.30 (dd, J=7.2, 3.6 Hz, 1H), 7.40 (s, 4H).

Additional Compounds that were Prepared by General Procedure E

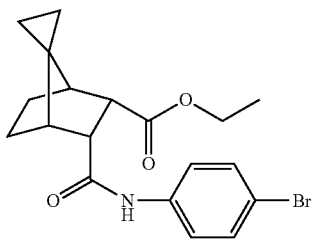

Compound 84

(+/−)-(1S,2R,3S,4R)-Ethyl 2-((4-bromophenyl)car-
bamoyl)spiro[bicyclo[2.2.1]heptane-7,1'-cyclopro-
pane]-3-carboxylate (Compound 84)

¹HNMR (300 MHz, CDCl₃): δ 0.50-0.65 (m, 4H), 1.09 (t, J=7.2 Hz, 3H), 1.50-1.85 (m, 5H), 2.20-2.31 (m, 1H), 3.10 (d, J=7.8 Hz, 1H), 3.45 (dd, J=7.2, 3.6 Hz, 1H), 3.99 (q, J=7.2 Hz, 2H), 7.42 (d, J=8.2 Hz, 2H), 7.63 (d, J=8.2 Hz, 2H).

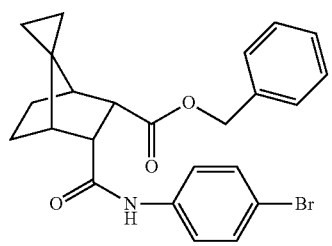

Compound 85

(+/−)-(1S,2R,3S,4R)-Benzyl 2-((4-bromophenyl)
carbamoyl)spiro[bicyclo[2.2.1]heptane-7,1'-cyclo-
propane]-3-carboxylate (Compound 85)

¹HNMR (300 MHz, CD₃COCD₃): δ 0.45-0.65 (m, 4H), 1.60-1.88 (m, 4H), 2.30-2.42 (m, 1H), 3.06-3.22 (m, 2H), 3.52 (dd, J=11.3, 4.5 Hz, 1H), 4.98 (ABq, J=8.5 Hz, 2H), 7.10-7.24 (m, 3H), 7.28 (d, J=6.7 Hz, 2H), 7.46 (d, J=8.2 Hz, 2H), 7.62 (d, J=8.2 Hz, 2H).

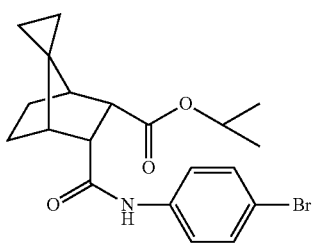

Compound 86

(+/−)-(1S,2R,3S,4R)-Isopropyl 2-((4-bromophenyl)
carbamoyl)spiro[bicyclo[2.2.1]heptane-7,1'-cyclo-
propane]-3-carboxylate (Compound 86)

A mixture of compound 10 (200 mg, 0.55 mmol), 2-iodopropane (935 mg, 5.5 mmol), NaHCO₃ (460 mg, 5.5 mmol) and DMF (5 mL) was stirred at RT for 48 h. Then the solvent was removed by distillation, crude product was crystallized using CH₂Cl₂ and hexane. The product (compound 86) was isolated as a white solid.

¹HNMR (300 MHz, CD₃COCD₃): δ 0.45-0.60 (m, 4H), 1.05 (d, J=6.3 Hz, 3H), 1.12 (d, J=6.3 Hz, 3H), 1.55-1.70 (m, 3H), 1.75-1.90 (m, 2H), 2.23-2.34 (m, 1H), 3.08 (d, J=11.4 Hz, 1H), 3.44 (dd, J=11.4, 4.4 Hz, 1H), 4.89 (septet, J=6.3 Hz, 1H), 7.43 (d, J=8.8 Hz, 2H), 7.64 (d, J=8.8 Hz, 2H).

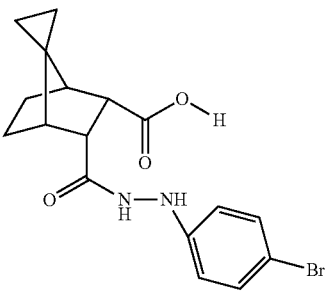

Compound 87

(+/−)-(1S,2R,3S,4R)-2-(2-(4-Bromophenyl)hydrazi-
necarbonyl)spiro[bicyclo[2.2.1]heptane-7,1'-cyclo-
propane]-3-carboxylic Acid (Compound 87)

To a solution of compound 2 (62 mg, 0.33 mmol), in CH₂Cl₂ (1 mL) was added 4-bromophenylhydrazine (CAS 41931-18-4) (61 mg, 0.33 mmol) in CH₂Cl₂ (2 mL). The reaction was stirred for 2 h at RT. The product (compound 87) separated as a white ppt, which was collected by filtration.

¹HNMR (300 MHz, CD₃OD): δ 0.50-0.70 (m, 4H), 1.60-1.85 (m, 5H), 2.10-2.20 (m, 1H), 3.20 (dd, J=8.4, 2.1 Hz, 1H), 3.40 (dd, J=8.4 Hz, 2.1 Hz, 1H), 6.73 (d, J=6.9 Hz, 2H), 7.24 (d, J=6.9 Hz, 2H).

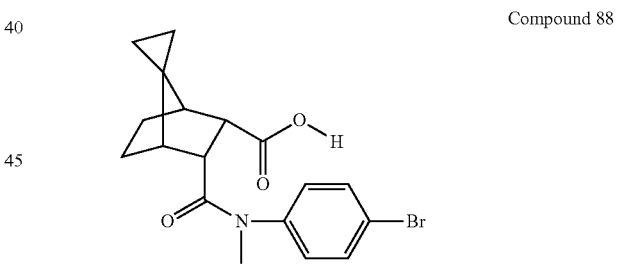

Compound 88

(1S,2R,3S,4R)-2-((4-bromophenyl)(methyl)carbam-
oyl)spiro[bicyclo[2.2.1]heptane-7,1'-cyclopropane]-
3-carboxylic acid (+/−)-(1S,2R,3S,4R)-2-((4-Bromophenyl)(methyl)
carbamoyl)spiro[bicyclo[2.2.1]heptane-7,1'-cyclo-
propane]-3-carboxylate (Compound 88)

To a cold (−50° C.) solution of 4-bromo N-methylaniline (564 mg, 3.03 mmol) in THF (5 mL) was added n-BuLi (2.5 M solution in hexane, 0.4 mL, 1 mmol). The reaction was warmed to RT and stirred for 30 min. To this turbid reaction mixture a solution of compound 2 (186 mg, 0.96 mmol) in THF (5 mL) was added and stirred for 2 h. After which time all the solvent was removed under reduced pressure. The crude solid was diluted with ice-cold 10% HCl (10 mL), ether (40 mL) and mixed well in a separatory funnel. The aq. layer was discarded, and the ether layer and the undissolved solid were collected and the solvent was removed under reduced pressure. This crude mixture was purified by reverse phase column chromatography and eluted with $CH_3CN:H_2O:TFA$ (90:9.9:0.1). The product (compound 86) was collected as colorless crystals.

$^1$HNMR (300 MHz, $CD_3OD$): δ 0.30-0.50 (m, 2H), 0.60-0.80 (m, 2H), 1.20-1.35 (m, 1H), 1.50-1.70 (m, 4H), 1.82 (br. s, 1H), 2.83 (d, J=5.4 Hz, 1H), 3.22 (s, 3H), 3.69 (br. s, 1H), 7.23 (d, J=8.4 Hz, 2H), 7.62 (d, J=8.4 Hz, 2H).

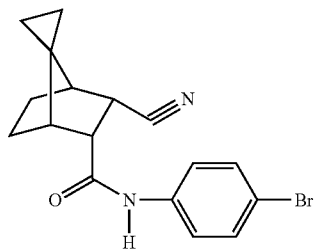

Compound 89

(+/−)-(1S,2R,3S,4R)—N-(4-Bromophenyl)-3-cyano-spiro[bicyclo[2.2.1]heptane-7,1'-cyclopropane]-2-carboxamide (Compound 89)

To a solution of compound 46 (50 mg, 0.14 mmol) in DMF (5 mL) was added 4A molecular sieves (100 mg) and stirred for 10 min. Cyanuric chloride (40 mg, 0.21 mmol) was added to the reaction and heated for 18 h at 100° C. Solvent was removed under reduced pressure and the crude mixture was purified by silicagel prep. TLC, $MeOH:CH_2Cl_2$ (1:49) was used as eluent. The product (compound 89) was isolated as a pale yellow solid.

$^1$HNMR (300 MHz, $CDCl_3$): δ 0.64 (br. s., 4H), 1.45-1.60 (m, 2H), 1.85-1.95 (m, 2H), 2.08 (br. s., 2H), 3.44 (br. s., 2H), 7.17 (d, J=8.2 Hz, 2H), 7.59 (d, J=8.2 Hz, 2H).

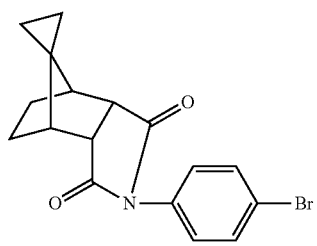

Compound 90

(3aR,4S,7R,7aS)-2-(4-Bromophenyl)-hexahydro-1H-spiro[4,7-methanoisoindole-8,1'-cyclopropane]-1,3 (2H)-dione (Compound 90)

A mixture of compound 10 (200 mg, 0.55 mmol), $K_2CO_3$ (110 mg, 0.83 mmol), Me2SO4 (126 mg, 1 mmol), acetone (10 mL) was heated to 80° C. 18 h. The solvent was removed under reduced pressure, and the solid was extracted with $CH_2Cl_2$ (40 mL). The $CH_2Cl_2$ layer was dried with $MgSO_4$ and solvent removed under reduced pressure. The crude reaction mixture was purified by silicagel column chromatography, using EtOAc:Hexane (3:7). Compound 90 was isolated as a white solid.

$^1$HNMR (300 MHz, $CD_3OD$): δ 0.55-0.75 (m, 4H), 1.47-1.55 (m, 3H), 1.85-2.04 (m, 3H), 3.50 (br. s., 2H), 7.21 (d, J=8.5 Hz, 2H), 7.65 (d, J=8.5 Hz, 2H).

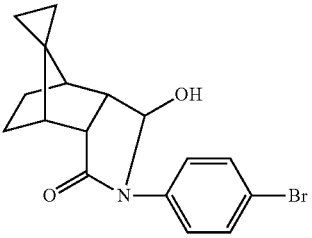

Compound 91

(+/−)-(3aR,4S,7R,7aS)-2-(4-Bromophenyl)-1-hydroxyhexahydro-1H-spiro[4,7-methanoisoindole-8, 1'-cyclopropane]-3(2H)-one (Compound 91)

A mixture of compound 90 (108 mg, 0.31 mmol), $NaBH_4$ (60 mg, 1.55 mmol) and MeOH and stirred for 18 h at 45° C. The solvent was removed under reduced pressure and the crude mixture was diluted with $CH_2Cl_2$ (40 mL). The organic layer was washed with $NaHCO_3$ in water, dried over $MgSO_4$ and filtered off. The solvent was removed under reduced pressure. The crude mixture was purified by silicagel prep. TLC using $MeOH:CH_2Cl_2$ (1:19). The product (compound 91) was isolated as a white solid.

$^1$HNMR (300 MHz, $CD_3OD$): δ 0.55-0.70 (m, 4H), 1.45-1.55 (m, 3H), 1.65-1.90 (m, 4H), 2.72 (dd, J=12.0, 6.0 Hz, 1H), 3.29 (dd, J=12.0, 6.0 Hz, 1H), 7.48 (d, J=8.8 Hz, 2H), 7.57 (d, J=8.8 Hz, 2H).

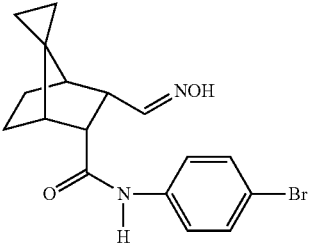

Compound 92

(+/−)-(1S,2R,3S,4R)—N-(4-Bromophenyl)-3-((hydroxyimino)methyl)spiro[bicyclo[2.2.1]heptane-7,1'-cyclopropane]-2-carboxamide (Compound 92)

A mixture of compound 91 (20 mg, 0.06 mmol), $K_2CO_3$ (17 mg, 0.12 mmol), $NH_2OH.HCl$ (4 mg, 0.06 mmol) and MeOH (5 mL) was heated to 60° C. for 72 h. After which time the solvent was removed under reduced pressure. The crude reaction mixture was purified by silicagel prep. TLC, using $MeOH:CH_2Cl_2$ (3:47). Compound 92 was isolated as a white solid.

$^1$HNMR (300 MHz, $CD_3OD$): δ 0.50-0.70 (m, 4H), 1.47-1.55 (m, 1H), 1.65-1.85 (m, 5H), 2.95 (dd, J=12.0, 6.0 Hz, 1H), 3.19 (dd, J=12.0, 6.0 Hz, 1H), 7.41 (d, J=8.8 Hz, 2H), 7.59 (d, J=8.8 Hz, 2H).

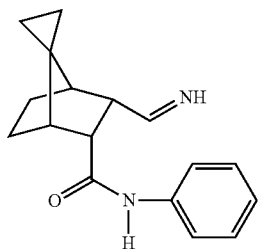

Compound 93

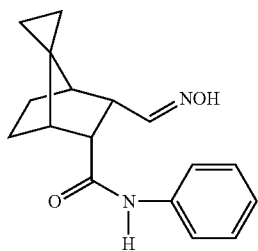

Compound 94

(+/−)-(1S,2R,3S,4R)-3-(Iminomethyl)-N-phenylspiro[bicyclo[2.2.1]heptane-7,1'-cyclopropane]-2-carboxamide (Compound 93) and (+/−)-(1S,2R,3S,4R)-3-((Hydroxyimino)methyl)-N-phenylspiro[bicyclo[2.2.1]heptane-7,1'-cyclopropane]-2-carboxamide (Compound 94)

A mixture of compound 92 (20 mg, 0.06 mmol), Pd—C (10%) (2 mg), AcOH (75 mg) in MeOH (10 mL) was hydrogenated under 50 psi hydrogen atmosphere for 18 h. After which time the solvent was removed under reduced pressure. The crude reaction was purified by silicagel prep TLC.

The faster moving product (compound 93) was isolated as a pale yellow solid and the slower moving product (compound 94) was isolated as a pale yellow syrup.

Compound 93: $^1$HNMR (300 MHz, CDCl$_3$): δ 0.45-0.65 (m, 4H), 1.45-1.60 (m, 2H), 1.55-1.80 (m, 3H), 1.85-1.90 (m, 1H), 2.55 (dd, J=10.7, 5.4 Hz, 1H), 3.23 (dd, J=10.7, 5.4 Hz, 1H), 7.17-7.25 (m, 2H), 7.34-7.45 (m, 3H).

Compound 94: $^1$HNMR (300 MHz, CDCl$_3$): δ 0.50-0.65 (m, 4H), 1.45-1.60 (m, 2H), 1.70-1.80 (m, 3H), 1.93-2.00 (m, 1H), 2.75 (dd, J=10.7, 5.4 Hz, 1H), 3.23 (m, 1H), 7.20-7.27 (m, 1H), 7.40 (t, J=8.2 Hz, 2H), 7.57 (d, J=8.2 Hz, 2H).

While this invention has been described with respect to these specific examples, it is understood that other modifications and variations are possible without departing from the spirit of the invention.

What is claimed is:
1. A compound of the structure:

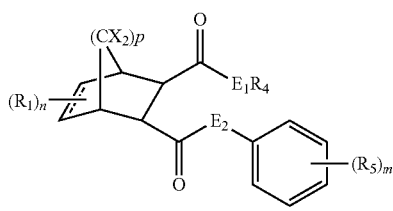

wherein:
- a dashed line represents the presence or absence of a bond;
- each $R_1$ is independently H, $C_1$-$C_6$ alkyl, $C_3$-$C_8$ cycloalkyl, or halide;
- $R_4$ is H or $C_1$-$C_6$ alkyl;
- each $R_5$ is independently H, $C_1$-$C_6$ alkyl, cycloalkyl, aryl, fused aryl, alkenyl, alkynyl, halide, hydroxy, alkoxy, trifluoromethyl, acetyl, —OCF$_3$, —SCF$_3$, nitroso, cyano, thioalkyl, —S(O)Me, —S(O)$_2$Me, —S(O)$_2$NH$_2$, or —C(O)OR$_6$, wherein $R_6$ is H or $C_1$-$C_6$ alkyl;
- each X is independently $C_1$-$C_6$ alkyl, $C_1$-$C_6$ alkoxy, or each X taken together forms a cycloalkyl moiety, or each X taken together forms a substituted double bond;
- $E_1$ is O or NH;
- $E_2$ is O or NR$_7$, wherein $R_7$ is H or $C_1$-$C_6$ alkyl;
- n is 0-2;
- m is 0-5; and
- p is 1 or 2;

or pharmaceutically acceptable salts, hydrates, solvates, tautomers, enantiomers, and diastereomers thereof.

2. The compound of claim 1 wherein $E_2$ is NR$_7$.

3. The compound of claim 1 of the structure

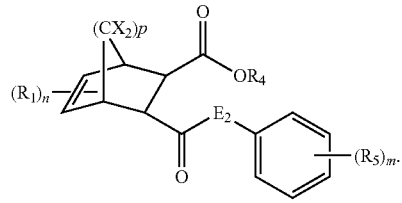

4. The compound claim 1 of the structure

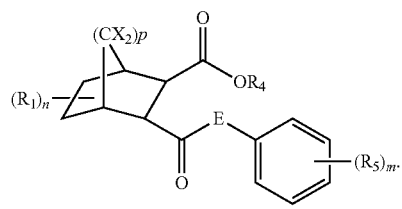

5. The compound of claim 1 wherein $R_5$ is H, $C_1$-$C_6$ alkyl, halide, or trifluoromethyl.

6. The compound of claim 1 wherein each X taken together forms a cyclopropyl moiety.

7. The compound of claim 1 having any one of the structures

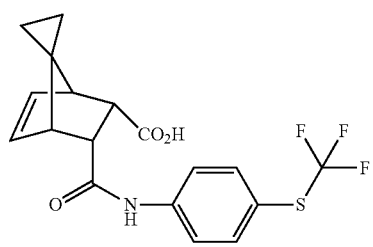

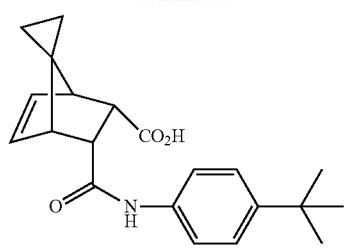
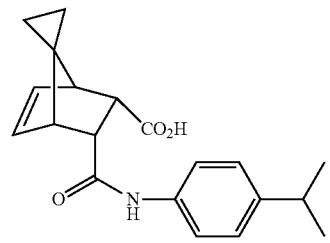
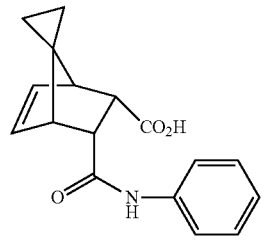
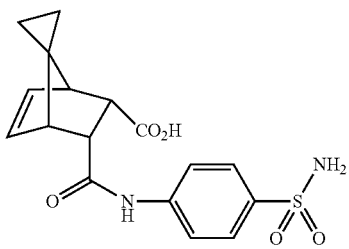
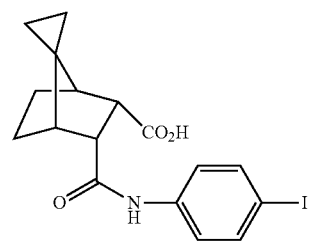
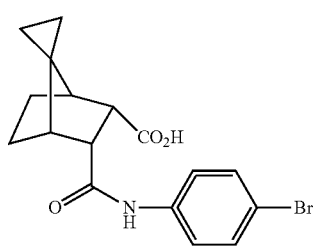
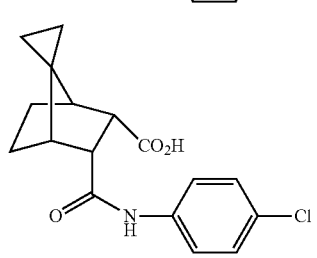
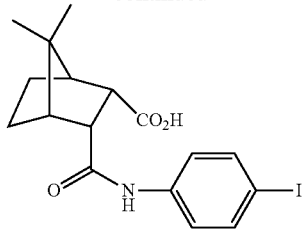
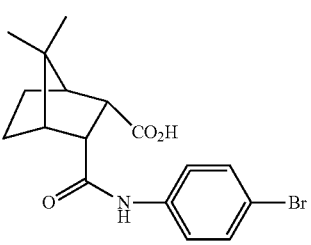
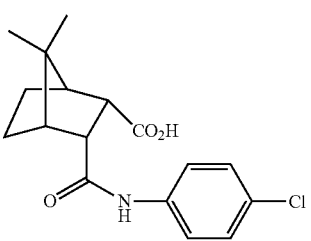
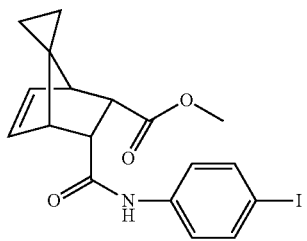
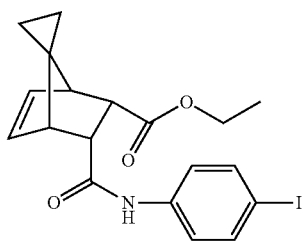
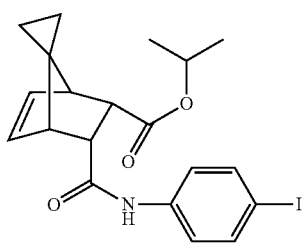

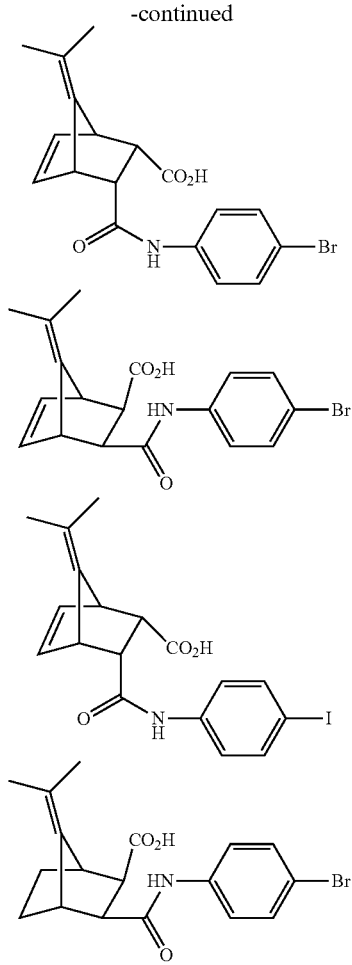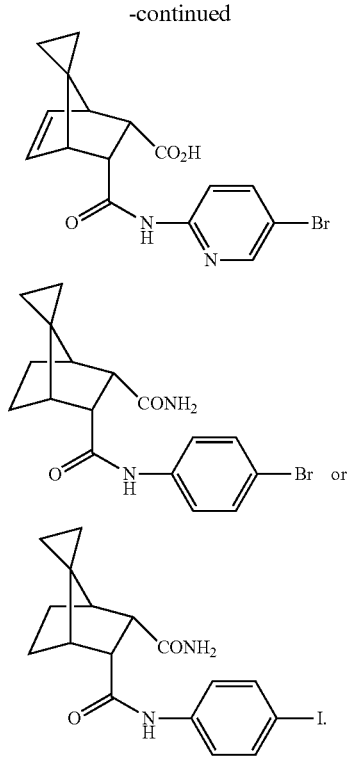
8. A composition comprising at least one compound according to claim 1, wherein the composition is a liquid which is ophthalmically acceptable.
* * * * *

UNITED STATES PATENT AND TRADEMARK OFFICE
CERTIFICATE OF CORRECTION

PATENT NO. : 8,618,163 B2
APPLICATION NO. : 13/168464
DATED : December 31, 2013
INVENTOR(S) : Richard L. Beard et al.

It is certified that error appears in the above-identified patent and that said Letters Patent is hereby corrected as shown below:

On the title page, item (56), under "Other Publications", in column 2, line 10,
delete "ofPlant" and insert -- of Plant --, therefor.

In the Specifications:

In column 1, line 33, delete "glucocotricoid" and insert -- glucocorticoid --, therefor.

In column 2, line 32, delete "$NR_S$," and insert -- $NR_7$, --, therefor.

In column 3, line 10, delete "$NR_S$," and insert -- $NR_7$, --, therefor.

In column 3, line 52, delete "$NR_S$," and insert -- $NR_7$, --, therefor.

In column 4, line 30, before "—S—," delete "—C(O)—,".

In column 6, line 5, delete "$NR_S$," and insert -- $NR_7$, --, therefor.

In column 6, line 14, after "$NR_7$" insert -- . --.

In column 11, line 22, after "trifluoromethyl" insert -- . --.

In column 14, lines 1-14, after " 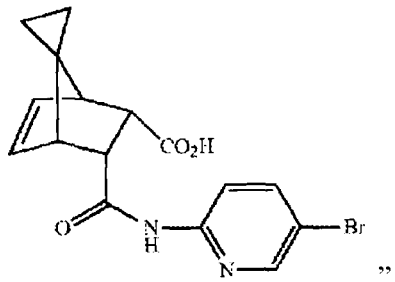 " insert -- . --.

In column 14, line 57, delete "$NR_S$," and insert -- $NR_7$, --, therefor.

In column 15, line 23, after "trifluoromethyl" insert -- . --.

In column 20, line 60, delete "RI," and insert -- RT, --, therefor.

In column 53, after the last Formula, delete "(EC50" and insert -- ($EC_{50}$ --, therefor.

Signed and Sealed this
Twenty-ninth Day of April, 2014

Michelle K. Lee
*Deputy Director of the United States Patent and Trademark Office*

CERTIFICATE OF CORRECTION (continued)
U.S. Pat. No. 8,618,163 B2

In column 55, line 30, delete "distcarate" and insert -- distearate --, therefor.

In column 57, line 39, after "solid" insert -- . --.

In column 60, lines 1-2, delete "bicycle" and insert -- bicyclo --, therefor.

In column 60, line 2, delete "1'cyclopropane" and insert -- 1'-cyclopropane --, therefor.

In column 61, line 35, delete "Absolute" and insert -- (Absolute --, therefor.

In column 62, line 47, delete "iodoanline" and insert -- iodoaniline --, therefor.

In column 62, line 55, after "1H)" insert -- . --.

In column 63, line 13, after "1H)" insert -- . --.

In column 69, line 14, delete "β3" and insert -- ((3 --, therefor.

In column 71, line 37, delete "β4" and insert -- ((4 --, therefor.

In column 72, line 22, delete "hz," and insert -- Hz, --, therefor.

In column 72, line 37, delete "β3" and insert -- ((3 --, therefor.

In column 72, line 67, after "1H)" insert -- . --.

In column 76, line 5, delete "Absolute" and insert -- (Absolute --, therefor.

In column 76, line 6, delete "Crystallography" and insert -- Crystallography) --, therefor.

In column 76, line 61, delete "N-5" and insert -- N5 --, therefor.

In column 77, line 14, delete "N-5" and insert -- N5 --, therefor.

In column 77, line 38, delete "N-5" and insert -- N5 --, therefor.

In column 77, line 61, delete "N-5" and insert -- N5 --, therefor.

In column 78, line 37, delete "$N^{2}$" and insert -- N2 --, therefor.

In column 79, line 41, delete "hz," and insert -- Hz, --, therefor.

In column 80, lines 46-47, delete "chromatrography" and insert -- chromatography --, therefor.

In column 81, line 15, delete "titutrated" and insert -- titrated --, therefor.

In column 81, line 34, delete "cyclopropan]" and insert -- cyclopropane] --, therefor In column 81, line 45, delete "(MgSO4)," and insert -- (MgSO$_4$), --, therefor.

In column 81, line 47, delete "chromatrography" and insert -- chromatography --, therefor In column 93, line 60, delete "Me2SO4" and insert -- Me$_2$SO$_4$ --, therefor In the Claims:

In column 96, line 38, in claim 4, delete "claim" and insert -- of claim --, therefor.